United States Patent
Han et al.

(10) Patent No.: US 7,528,136 B2
(45) Date of Patent: May 5, 2009

(54) PROLINAMIDE DERIVATIVES AS NK3 ANTAGONISTS

(75) Inventors: Bo Han, Shanghai (CN); Henner Knust, Rheinfelden (DE); Matthias Nettekoven, Grenzach-Wyhlen (DE); Hasane Ratni, Habsheim (FR); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/129,718

(22) Filed: May 30, 2008

(65) Prior Publication Data

US 2008/0306086 A1    Dec. 11, 2008

(30) Foreign Application Priority Data

Jun. 7, 2007   (EP) .................... 07109781

(51) Int. Cl.
| | | |
|---|---|---|
| *A61K 31/496* | (2006.01) | |
| *A61K 31/4725* | (2006.01) | |
| *A61K 31/401* | (2006.01) | |
| *C07D 401/06* | (2006.01) | |
| *C07D 207/16* | (2006.01) | |
| *C07D 487/10* | (2006.01) | |

(52) U.S. Cl. .................. 514/254.01; 514/307; 514/326; 544/372; 546/17; 546/20; 546/146; 546/213

(58) Field of Classification Search ........................ None
See application file for complete search history.

(56) References Cited

FOREIGN PATENT DOCUMENTS

WO    WO 2004/056799    7/2004

OTHER PUBLICATIONS

Tooney et al., Neurosci. Letters, vol. 283 pp. 185-188 (2000).
Giardina et al., Exp. Opin. Ther. Patents vol. 10, pp. 939-960 (2000).
Jung et al., Neuroscience vol. 74 pp. 403-414 (1996).
Marco et al., Neuropeptides vol. 32, pp. 481-488 (1998).
Kamali, F., Current Opinion in Investigational Drugs, vol. 2(7) pp. 950-956 (2001).
Walpole, C et al, *Jour. of Med. Chem.*, 41:17 (1998) 3159-3173 XP000972902.

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to a compound of formula I

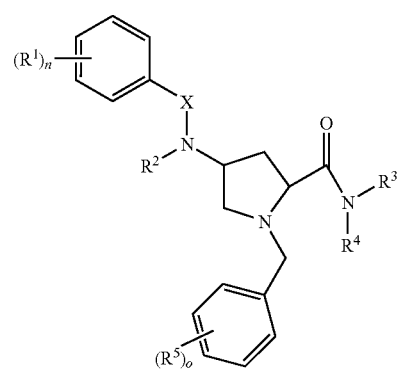

wherein
$R^1$,
$R^2$,
$R^3$, $R^4$, $R^5$,
X, n, and o are as defined herein and to a pharmaceutically acceptable acid addition salt thereof which are high potential NK-3 receptor antagonists for the treatment of depression, pain, psychosis, Parkinson's disease, schizophrenia, anxiety and attention deficit hyperactivity disorder (ADHD).

16 Claims, No Drawings

PROLINAMIDE DERIVATIVES AS NK3 ANTAGONISTS

PRIORITY TO RELATED APPLICATION(S)

This application claims the benefit of European Patent Application No. 07109781.0, filed Jun. 7, 2007, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH— terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Recources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956 956 and *Psychiatric Disorders Study* 4, *Schizophrenia*, June 2003, Decision Recources, Inc., Waltham, Mass.).

SUMMARY OF THE INVENTION

The present invention provides a compound of formula I

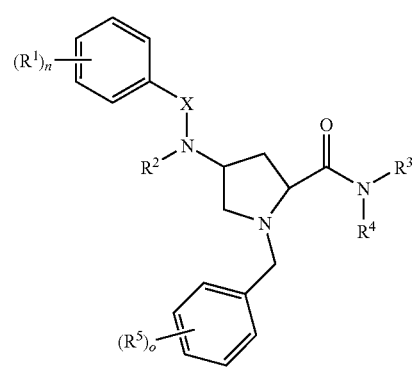

wherein $R^1$ is hydrogen, halogen, lower alkyl, lower alkyl substituted by halogen, lower alkoxy, or lower alkoxy substituted by halogen;

$R^2$ is hydrogen or lower alkyl;

$R^3$ and $R^4$ together with the N-atom to which they are attached form a non aromatic heterocyclic group, selected from

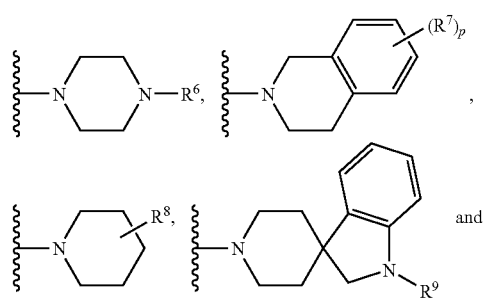

-continued

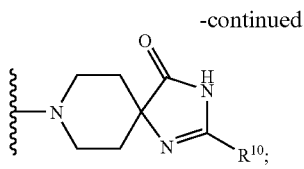

$R^5$ is hydrogen or halogen;
$R^6$ is phenyl, unsubstituted or substituted by cyano, halogen, lower alkyl, lower alkoxy, $CF_3$, —$(CH_2)_2$O-lower alkyl, C(O)-lower alkyl or C(O)O-lower alkyl, or is pyridinyl, unsubstituted or substituted by $CF_3$, or is —C(O)-phenyl;
$R^7$ is hydrogen or lower alkoxy;
$R^8$ is phenyl, lower alkyl or —C(O)O-lower alkyl;
$R^9$ is hydrogen or $S(O)_2$-lower alkyl;
$R^{10}$ is hydrogen or cycloalkyl;
X is —$CH_2$— or —C(O)—;
p is 1 or 2;
n is 1, 2 or 3; and
o is 1 or 2;

or a pharmaceutically acceptable acid addition salt thereof.

The invention includes all sterioisomeric forms, including individual diastereoisomers and enantiomers of the compound of formula (I) as well as racemic and non-racemic mixtures thereof.

The present invention also provides pharmaceutical compositions containing a compound of formula I or a pharmaceutically acceptable acid addition salt thereof. The invention further provides methods for the manufacture of the compounds and compositions of the invention.

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes a lower alkyl group as defined above, wherein at least one hydrogen atom is replaced by a halogen atom, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "lower alkoxy" denotes a group having a lower alkyl group as defined above that is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes a lower alkoxy group as defined above wherein at least one hydrogen atom is replaced by a halogen atom. Preferred lower alkoxy substituted by halogen groups are groups having 1-4 carbon atoms.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclpentyl, cyclohexyl, cycloheptyl, and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Compounds of formula I, wherein X is —$CH_2$— are preferred. Especially preferred compounds from this group are those, wherein $R^3/R^4$ form together with the N-atom to which they are attached a piperazine ring, which is substituted by $R^6$.

The preferred $R^6$-substitution is phenyl, substituted by cyano, for example the following compounds:
2-{4-[(2S,4S)-1-benzyl-4-(2,4-difluoro-benzylamino)-pyrrolidine-2-carbonyl]-piperazin-1-yl}-benzonitrile,
2-(4-{(2S,4S)-1-benzyl-4-[(3,5-bis-trifluoromethyl-benzyl)-methyl-amino]-pyrrolidine-2-carbonyl}-piperazin-1-yl)-benzonitrile,
2-{4-[(2S,4S)-1-benzyl-4-(3,5-dimethoxy-benzylamino)-pyrrolidine-2-carbonyl]-piperazin-1-yl}-benzonitrile,
2-{4-[(2S,4S)-1-benzyl-4-(2-trifluoromethyl-benzylamino)-pyrrolidine-2-carbonyl]-piperazin-1-yl}-benzonitrile,
2-{4-[(2S,4S)-1-benzyl-4-(2-chloro-5-trifluoromethyl-benzylamino)-pyrrolidine-2-carbonyl]-piperazin-1-yl}-benzonitrile,
2-{4-[(2S,4S)-1-benzyl-4-(3-chloro-benzylamino)-pyrrolidine-2-carbonyl]-piperazin-1-yl}-benzonitrile,
2-{4-[(2S,4S)-1-benzyl-4-(3-chloro-4-fluoro-benzylamino)-pyrrolidine-2-carbonyl]-piperazin-1-yl}-benzonitrile,
2-{4-[(2S,4S)-1-benzyl-4-(3,4-dichloro-benzylamino)-pyrrolidine-2-carbonyl]-piperazin-1-yl}-benzonitrile,
2-{4-[(2S,4S)-1-benzyl-4-(3-chloro-2-fluoro-benzylamino)-pyrrolidine-2-carbonyl]-piperazin-1-yl}-benzonitrile,
2-{4-[4-(2,4-difluoro-benzylamino)-1-(3-fluoro-benzyl)-pyrrolidine-2-carbonyl]-piperazin-1-yl}-benzonitrile and
2-{4-[(2S,4R)-1-benzyl-4-(2,4-difluoro-benzylamino)-pyrrolidine-2-carbonyl]-piperazin-1-yl}-benzonitrile.

A further preferred $R^6$-substitution is phenyl, substituted by $CF_3$, for example the following compounds:
[(2S,4S)-1-benzyl-4-(2,4-difluoro-benzylamino)-pyrrolidin-2-yl]-[4-(3-trifluoromethyl-phenyl)-piperazin-1-yl]-methanone,
{(2S,4S)-1-benzyl-4-[(3,5-bis-trifluoromethyl-benzyl)-methyl-amino]-pyrrolidin-2-yl}-[4-(3-trifluoromethyl-phenyl)-piperazin-1-yl]-methanone,
[(2S,4S)-4-[(3,5-bis-trifluoromethyl-benzyl)-methyl-amino]-1-(3-chloro-benzyl)-pyrrolidin-2-yl]-[4-(3-trifluoromethyl-phenyl)-piperazin-1-yl]-methanone and
[(2S,4R)-1-benzyl-4-(2,4-difluoro-benzylamino)-pyrrolidin-2-yl]-[4-(3-trifluoromethyl-phenyl)-piperazin-1-yl]-methanone.

Further preferred $R^6$-substitution is phenyl, substituted by halogen, for example the following compounds:
[(2S,4S)-1-benzyl-4-(2,4-difluoro-benzylamino)-pyrrolidin-2-yl]-[4-(4-fluoro-phenyl)-piperazin-1-yl]-methanone or
[(2S,4S)-1-benzyl-4-(2,4-difluoro-benzylamino)-pyrrolidin-2-yl]-[4-(2-chloro-phenyl)-piperazin-1-yl]-methanone.

A further preferred $R^6$-substitution is phenyl, unsubstituted or substituted by lower alkoxy, for example the following compounds:

[(2S,4S)-1-benzyl-4-(2,4-difluoro-benzylamino)-pyrrolidin-2-yl]-(4-phenyl-piperazin-1-yl)-methanone and
[(2S,4S)-1-benzyl-4-(2,4-difluoro-benzylamino)-pyrrolidin-2-yl]-[4-(2-methoxy-phenyl)-piperazin-1-yl]-methanone.

Preferred are further compounds of formula I, wherein X is —CH$_2$— and R$^3$/R$^4$ form together with the N-atom to which they are attached the group 3,4-dihydro-1H-isoquinolin, substituted by R$^7$, for example the following compound:
[(2S,4S)-1-benzyl-4-(2,4-difluoro-benzylamino)-pyrrolidin-2-yl]-(6,7-dimethoxy-3,4-dihydro-1H-isoquinolin-2-yl)-methanone.

Further preferred compounds are those, wherein X is —C(O)—, for example the following compounds:
N-{(3S,5S)-1-benzyl-5-[4-(2-cyano-phenyl)-piperazine-1-carbonyl]-pyrrolidin-3-yl}-2-chloro-benzamide,
N-{(3S,5S)-1-benzyl-5-[4-(2-cyano-phenyl)-piperazine-1-carbonyl]-pyrrolidin-3-yl}-3,5-dichloro-benzamide,
N-{(3S,5S)-1-benzyl-5-[4-(2-cyano-phenyl)-piperazine-1-carbonyl]-pyrrolidin-3-yl}-2-trifluoromethyl-benzamide and
N-{(3S,5S)-1-benzyl-5-[4-(2-cyano-phenyl)-piperazine-1-carbonyl]-pyrrolidin-3-yl}-2-methoxy-benzamide.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises a) cleaving off a protecting group from a compound of formula

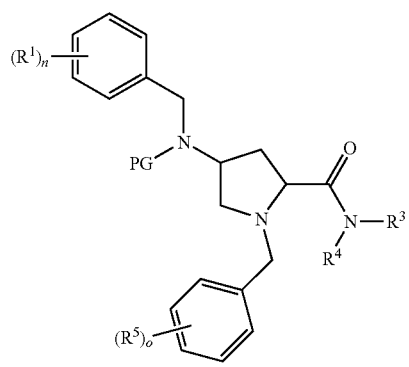

2 to obtain a compound of formula

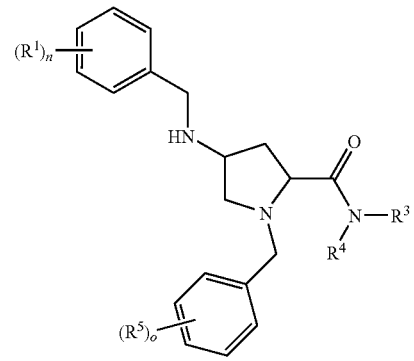

I-1 wherein the protecting group is selected from the group consisting of tertbutoxycarbonyl or carbamic acid 2,2,2-trichloro-ethyl ester, and the other substituents are as described above, or b) reacting a compound of formula

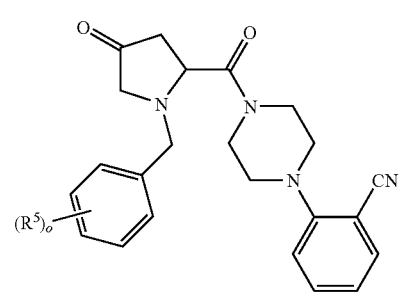

3 with a compound of formula

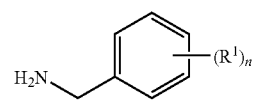

to obtain a compound of formula

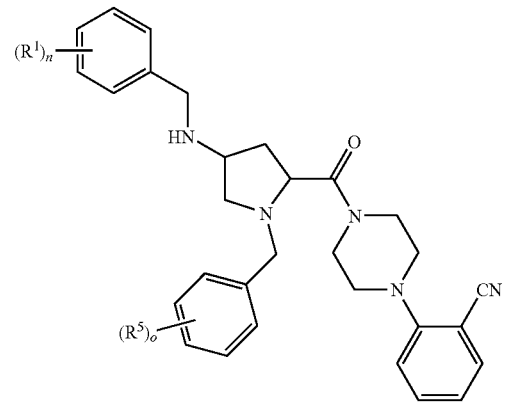

I-2 wherein the substituents are as described above, or c) reacting a compound of formula

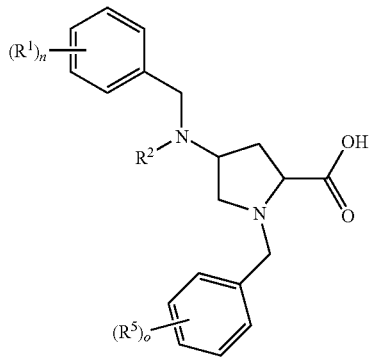

with an amine of formula

NHR³R⁴ to obtain a compound of formula

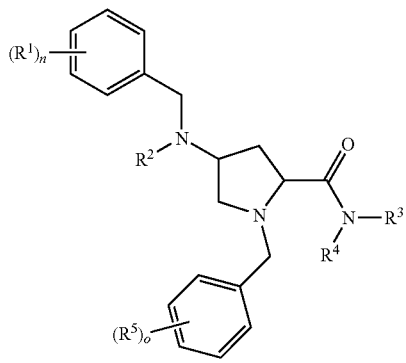

wherein the substituents are as described above, or d) reacting a compound of formula

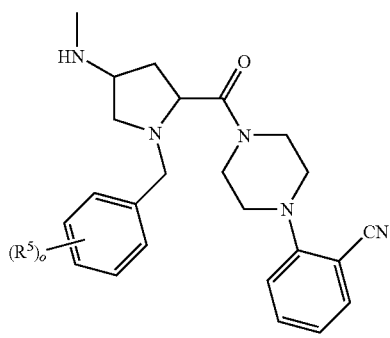

with a compound of formula

to obtain a compound of formula

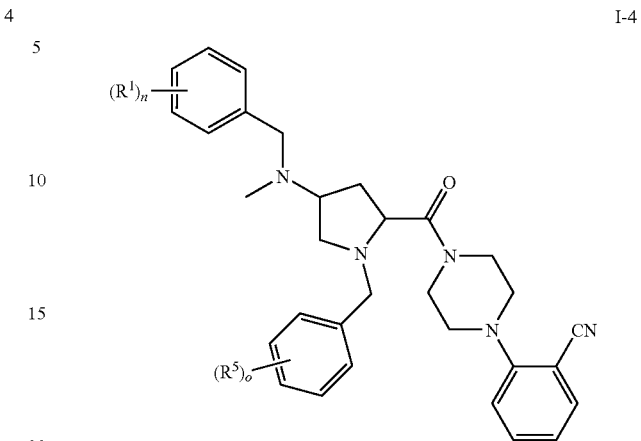

wherein the substituents are as described above, or e) reacting a compound of formula

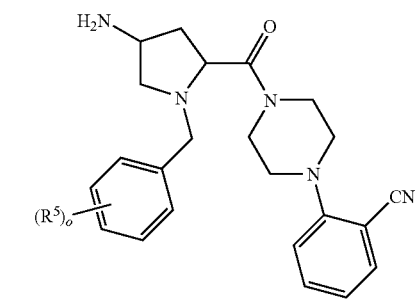

with a compound of formula

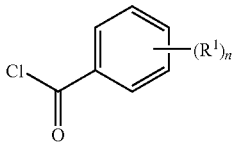

to obtain a compound of formula

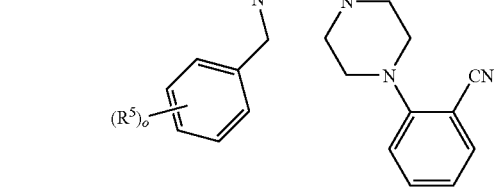

wherein the substituents are as described above, and, if desired, converting a compound of formula I into a pharmaceutically acceptable salt.

The preparation of compounds of formula I is further described in more detail in schemes 1-7 and in examples 1-98.

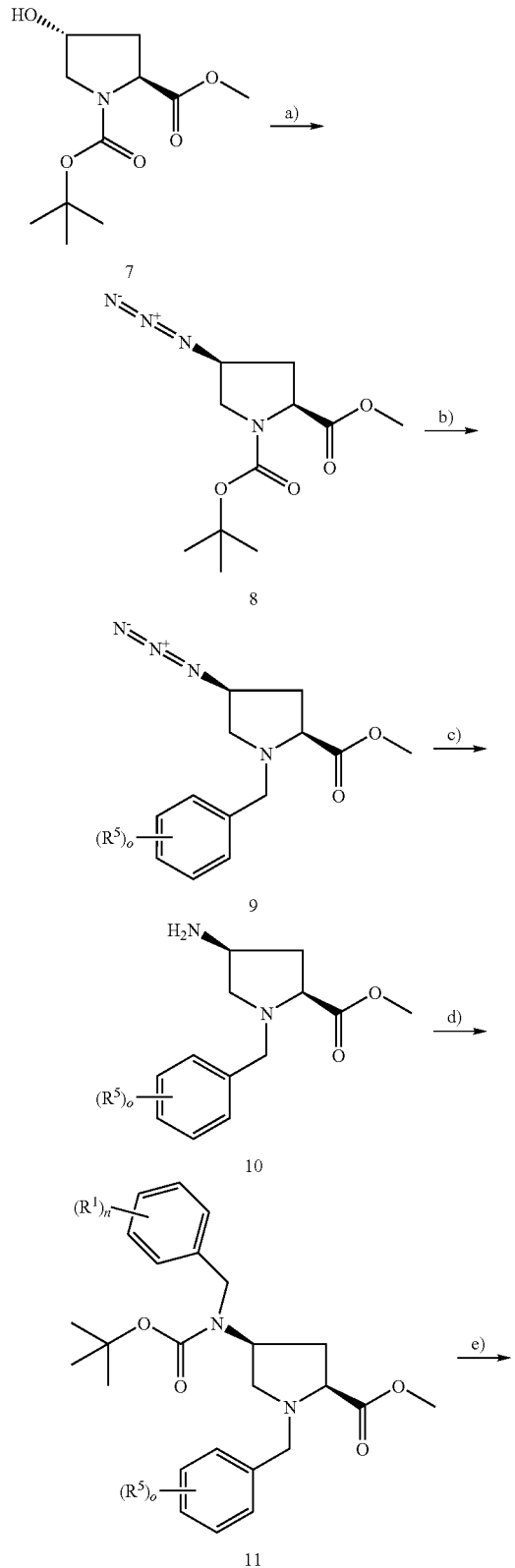

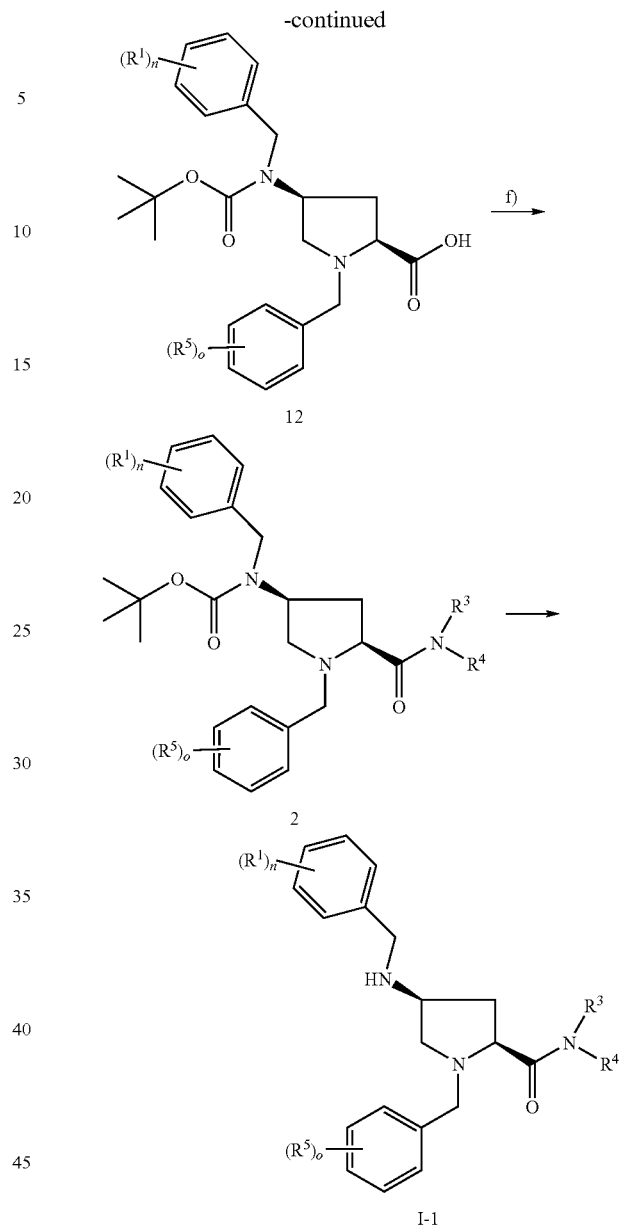

a) To a solution of trans-N-Boc-4-hydroxy-L-proline methyl ester (7) in pyridine and dry DCM at 0° C. is added 4-methyl-benzenesulfonyl chloride. After adding, the mixture is refluxed overnight. The solvent is evaporated and then the residue is dissolved in $CH_2Cl_2$. After removal of solvent, the crude 4-(toluene-4-sulfonyloxy)-pyrrolidine-1,2-dicarboxylic acid 1-tert-butyl ester 2-methyl ester is obtained, which is used in the following reaction without further purification. To a solution of 4-(toluene-4-sulfonyloxy)-pyrrolidine-1,2-dicarboxylic acid 1-tert-butyl ester 2-methyl ester thus obtained above in dry DMF is added $NaN_3$ in one portion, and the reaction mixture is stirred at about 50° C. for 5 h. The resulting mixture is purified to give 4-azido-pyrrolidine-1,2-dicarboxylic acid 1-tert-butyl ester 2-methyl ester (8).

b) A mixture of 4-azido-pyrrolidine-1,2-dicarboxylic acid 1-tert-butyl ester 2-methyl ester in $CF_3COOH/CH_2Cl_2$ is stirred overnight at room temperature. To a solution of the obtained product in DCM is added a corresponding unsubstituted or halogen-substituted benzaldehyde, acetic acid and $NaBH(OAc)_3$. After stirred overnight, the reaction mixture is purified to afford the corresponding product 4-azido-1-benzyl-pyrrolidine-2-carboxylic acid methyl ester (9).

c) To a solution of 4-azido-1-benzyl-pyrrolidine-2-carboxylic acid methyl ester (9) in THF under $N_2$ is added triphenylphosphine and water. The mixture is refluxed with stirring for about 6 h. After removal of THF, the residue is dissolved in $Et_2O$, treated with HCl, stirred for 5 min, and extracted with $Et_2O$. The aqueous solution is then treated with $NaHCO_3$ and extracted, dried and concentrated to afford product 4-amino-1-benzyl-pyrrolidine-2-carboxylic acid methyl ester (10).

d) To a solution of (10) and a benzaldehyde (unsubstituted or substituted by $R^1$) in DCM are added $MgSO_4$, AcOH, and then $NaBH_3CN$. The reaction mixture is stirred overnight, and then diluted with DCM. The organic solution is washed with $NaHCO_3$, dried and concentrated. The residue is dissolved in water, treated with $(Boc)_2O$, and then stirred overnight. The reaction mixture is extracted with DCM, dried, and concentrated to give product 1-benzyl-4-[tert-butoxycarbonyl-(benzyl)-amino]-pyrrolidine-2-carboxylic acid methyl ester (11).

e) To a solution of 1-benzyl-4-[tert-butoxycarbonyl-(benzyl)-amino]-pyrrolidine-2-carboxylic acid methyl ester (11) in $CH_3OH$ is added LiOH, and the solution is stirred overnight at rt. After removal of solvent, the residue is dissolved in water, acidified until PH=5, and then extracted with EA, and concentrated to afford the product 1-benzyl-4-[tert-butoxycarbonyl-(benzyl)-amino]-pyrrolidine-2-carboxylic acid (12).

f) The mixture of (12), N-hydroxybenzotriazole and 2-piperazin-1-yl-benzonitrile, triethylamine in dry dichloromethane is stirred overnight at rt, and then treated with trifluoroacetic acid. The resulting mixture is stirred at room temperature for another 5 h and concentrated. The residue was purified to afford the compound of formula I-1.

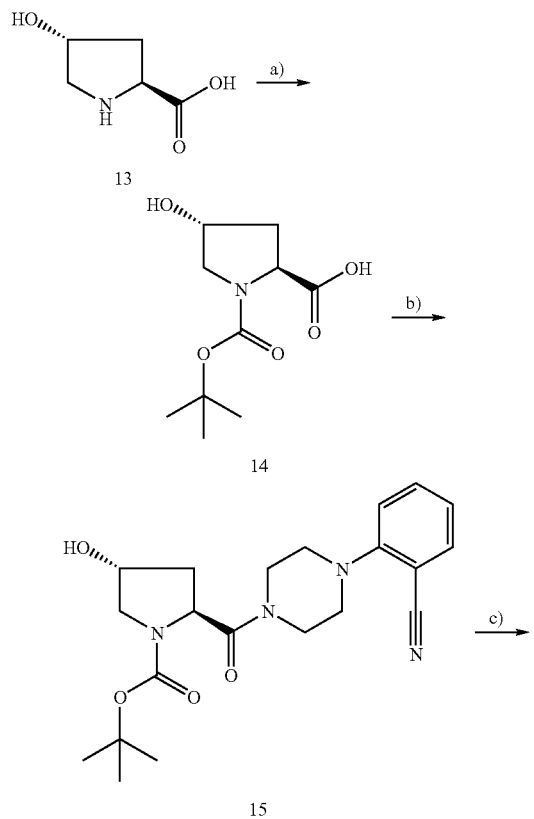

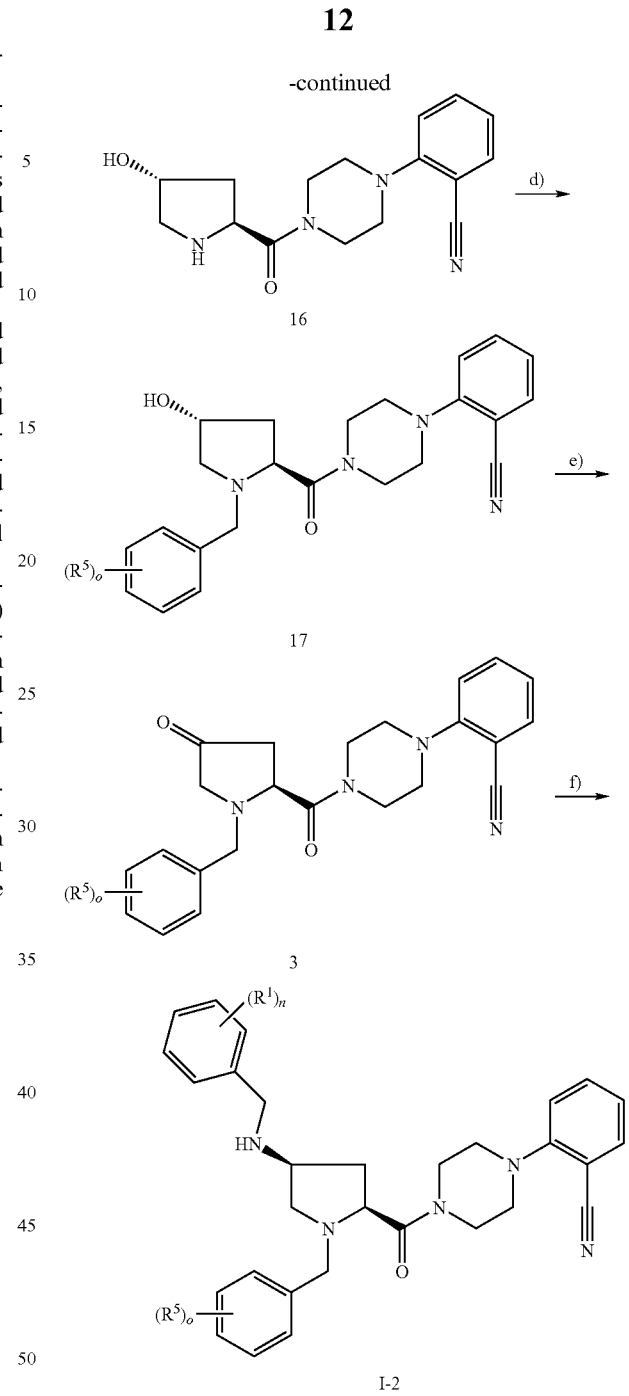

a) A solution of L-hydroxyproline in $Na_2CO_3$ is added dropwise to a solution of Boc-anhydride in THF/dioxane, and the mixture is stirred overnight. After removal of THF, the mixture is then washed with $Et_2O$, cooled to 0 degree, and acidified to PH=2 with HCl. The solution is extracted and the organic layer is dried and concentrated to afford 4-hydroxy-pyrrolidine-1,2-dicarboxylic acid 1-tert-butyl ester (14).

b) The mixture of 4-hydroxy-pyrrolidine-1,2-dicarboxylic acid 1-tert-butyl ester, EDC.HCl, HOBt, 2-piperazin-1-yl-benzonitrile and $Et_3N$ in DCM is stirred overnight. After removal of solvent, the residue is purified to afford the product 2-[4-(2-cyano-phenyl)-piperazie-1-carbonyl]-4-hydroxy-pyrrolidine-1-carboxylic acid tert-butyl ester (15).

c) 2-[4-(2-cyano-phenyl)-piperazie-1-carbonyl]-4-hydroxy-pyrrolidine-1-carboxylic acid tert-butyl ester is dissolved in DCM/CF$_3$COOH and stirred overnight. The solution is concentrated to afford 2-[4-(4-hydroxy-pyrrolidine-2-carbonyl)-piperazin-1-yl]-benzonitrile (16).

d) 2-[4-(4-hydroxy-pyrrolidine-2-carbonyl)-piperazin-1-yl]-benzonitrile is dissolved in DCM, and then benzaldehyde (unsubstituted or substituted by R$^5$) and NaBH(OAc)$_3$ is added. After stirred overnight, the reaction mixture is diluted with DCM, washed with NaHCO$_3$, dried, concentrated and purified to afford the corresponding 2-[4-(1-benzyl-4-hydroxy-pyrrolidine-2-carbonyl)-piperazin-41-yl]-benzonitrile (17).

e) Oxalyl chloride is added dropwise to a solution of anhydrous DCM and DMSO at −78 degree. The reaction mixture is allowed to stirred for about 30 min, then a solution of alcohol in DCM is added to keep the reaction temperature below −60 degree. Upon complete addition the reaction mixture is allowed to stir at −78 degree for about 2 h; then triethylamine is added. After complete addition, the mixture is allowed to be warmed to RT, and stirred overnight. After water is added to the reaction mixture, the pH is adjusted to 10 with NaHCO$_3$, and the product is extracted, washed, dried concentrated to afford 2-[4-(1-benzyl-4-oxo-pyrrolidine-2-carbonyl)-piperazin-41-yl]-benzonitrile (3).

f) 2-[4-(1-Benzyl-4-oxo-pyrrolidine-2-carbonyl)-piperazin-41-yl]-benzonitrile and 3,5-bis-trifluoromethyl-benzylamine are dissolved in DCM, then acetic acid and NaBH(OAc)$_3$ is added. After stirred for about 3 hours the reaction mixture is diluted, washed, dried and concentrated to afford 2-{4-[(2S,4S)-1-benzyl-4-(3,5-bis-trifluoromethyl-benzylamino)-pyrrolidine-2-carbonyl]-piperazin-1-yl}-benzonitrile (I-2).

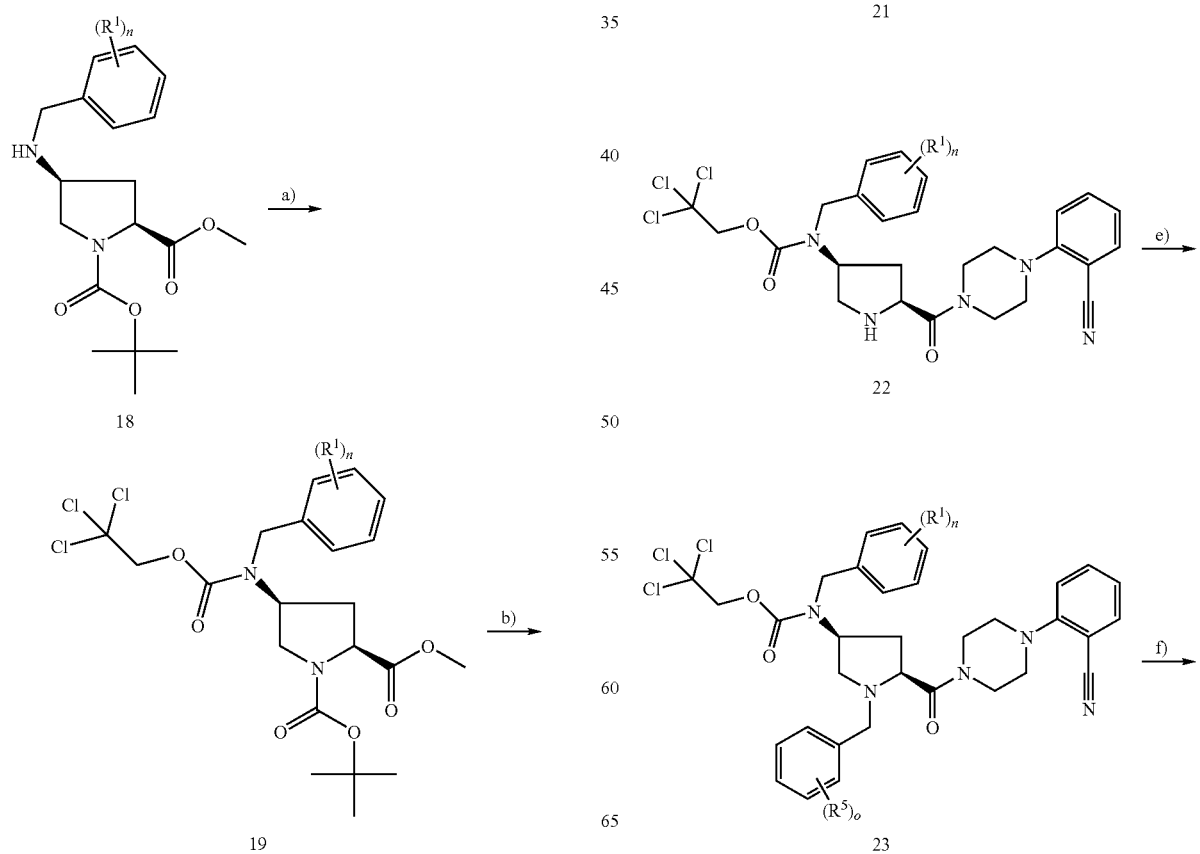

-continued

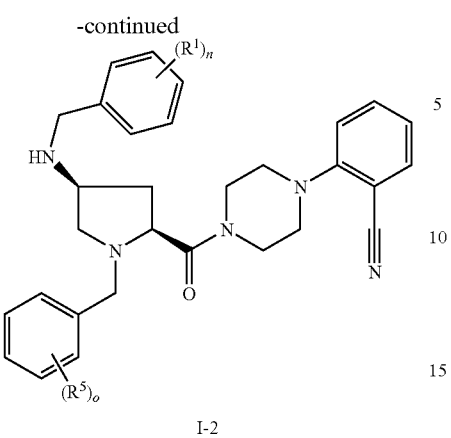

I-2 a) To a solution of a corresponding 4-[(benzylamino)]-pyrrolidine-1,2-dicarboxylic acid 1-tert-butyl ester 2-methyl ester in DCM, cooled to 0 degree is added TrocCl and TEA. The mixture is stirred overnight, washed with Na$_2$CO$_3$, brine, dried and concentrated in vacuo to give 4-[(benzyl)-(2,2,2-trichloro-ethoxycarbonyl)-amino]-pyrrolidine-1,2-dicarboxylicacid 1-tert-butyl ester 2-methyl ester (19).

b) To a solution of 4-[(benzyl)-(2,2,2-trichloro-ethoxycarbonyl)-amino]-pyrrolidine-1,2-dicarboxylicacid 1-tert-butyl ester 2-methyl ester in MeOH, cooled to 0 degree is added LiOH, and the mixture is stirred overnight. After removal of the solvent, the residue is acidified with HCl. The aqueous layer is extracted with EA, and the organic solution is dried, concentrated and purified to afford 4-[(benzyl)-(2,2,2-trichloro-ethoxycarbonyl)-amino]-pyrrolidine-1,2-dicarboxylicacid 1-tert-butyl ester (20).

c) To a solution of 4-[(benzyl)-(2,2,2-trichloro-ethoxycarbonyl)-amino]-pyrrolidine-1,2-dicarboxylicacid 1-tert-butyl ester, HOBt, 1-(2-cyanophenyl)piperazine in DCM are added Et$_3$N and EDC.HCl. The mixture is stirred overnight, then washed with citric acid, Na$_2$CO$_3$, brine, dried and concentrated to give 2-[4-(2-cyano-phenyl)-piperazine-1-carbonyl]-4-[(benzyl)-(2,2,2-trichloroethoxycarbonyl)-amino]-pyrrolidine-1-carboxylic acid tert-butyl ester (21)

d) A mixture of 2-[4-(2-cyano-phenyl)-piperazine-1-carbonyl]-4-[(benzyl)-(2,2,2-trichloroethoxycarbonyl)-amino]-pyrrolidine-1-carboxylic acid tert-butyl ester and CF$_3$COOH are stirred at rt for about 5 h, and then concentrated to give {5-[4-(2-cyano-phenyl)-piperazine-1-carbonyl]-pyrrolidin-3-yl}-(benzyl)-carbamic acid 2,2,2-trichloro-ethyl ester (22).

e) A mixture of {5-[4-(2-cyano-phenyl)-piperazine-1-carbonyl]-pyrrolidin-3-yl}-(benzyl)-carbamic acid 2,2,2-trichloro-ethyl ester, a corresponding benzaldehyde and acetic acid (cat.) in DCM is stirred for 20 min, and then NaBH(OAc)$_3$ is added. The reaction mixture is stirred overnight, and is concentrated to give {1-(benzyl)-5-[4-(2-cyano-phenyl)-piperazine-1-carbonyl]-pyrrolidin-3-yl}-(2,4-difluoro-benzyl)-carbamic acid 2,2,2-trichloro-ethyl ester (23).

f) {1-(Benzyl)-5-[4-(2-cyano-phenyl)-piperazine-1-carbonyl]-pyrrolidin-3-yl}-(2,4-difluoro-benzyl)-carbamic acid 2,2,2-trichloro-ethyl ester and Zn is dissolved in MeOH, and PH is adjust to 5-6 using acetic acid. The mixture is heated to reflux and stirred for about 30 min. After removal of methanol, the residue is purified to afford final product of formula I-2.

Scheme 4

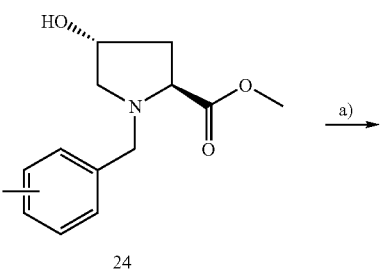
24

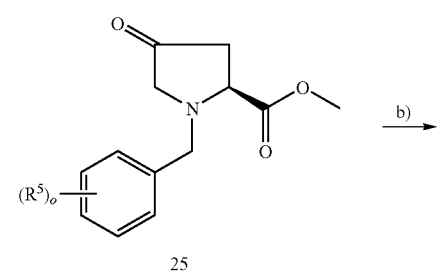
25

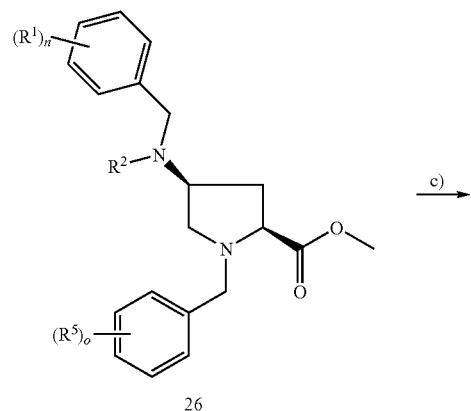
26

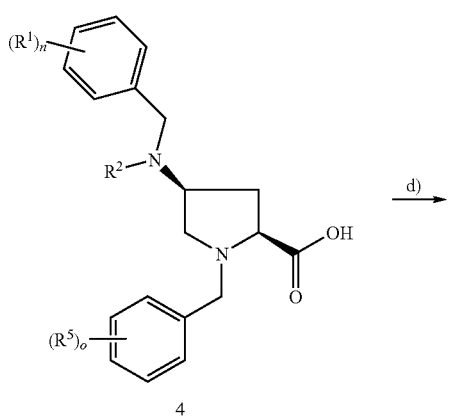
4

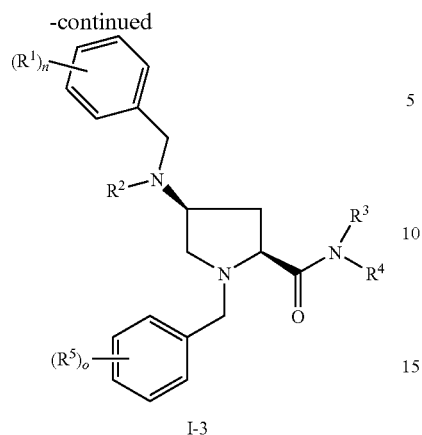

I-3 a) A solution of a corresponding 1-benzyl-4-hydroxy-pyrrolidine-2-carboxylic acid methyl ester in DCM, cooled at 0° C. is treated with trichloroisocyanuric acid and TEMPO, and then the reaction mixture is stirred at 0° C. for about 1 h. The mixture is diluted with DCM and washed with $NaHCO_3$, HCl, and brine. The organic layer is dried and concentrated to afford the product 1-benzyl-4-oxo-pyrrolidine-2-carboxylic acid methyl ester (25)

b) 1-Benzyl-4-oxo-pyrrolidine-2-carboxylic acid methyl ester and a corresponding benzylamine are dissolved in DCM, acetic acid and $NaBH(OAc)_3$ is then added. After stirred for about 3 hours the reaction mixture is diluted with DCM, washed, dried and concentrated. The residue is purified to afford 1-benzyl-4-(benzylamino)-pyrrolidine-2-carboxylic acid methyl ester (26).

c) 1-Benzyl-4-(benzylamino)-pyrrolidine-2-carboxylic acid methyl ester and LiOH are dissolved in $THF/H_2O$, and then stirred overnight. After removal of solvent, the residue is neutralized to PH=6-7, and then extracted by EA. The organic layer is washed with water and brine, dried, and concentrated to afford 1-benzyl-4-(benzylamino)-pyrrolidine-2-carboxylic acid (4).

d) The mixture of 1-benzyl-4-(benzylamino)-pyrrolidine-2-carboxylic acid, 1-ethyl-3-(3-dimethylaminopropyl)-carbodiimide hydrochloride, N-hydroxybenzotriazole, a corresponding amine of formula $NHR^3R^4$, triethylamine in dichloromethane is stirred overnight, and then concentrated. The residue is purified to afford a compound of formula I-3.

Scheme 5

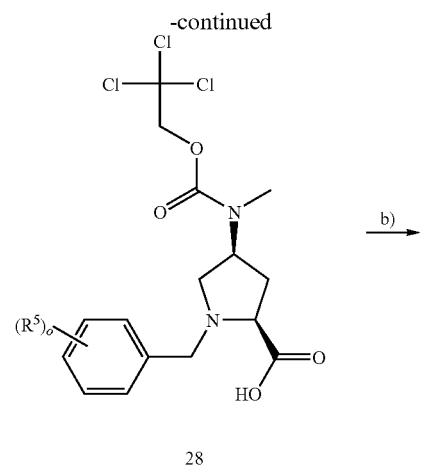

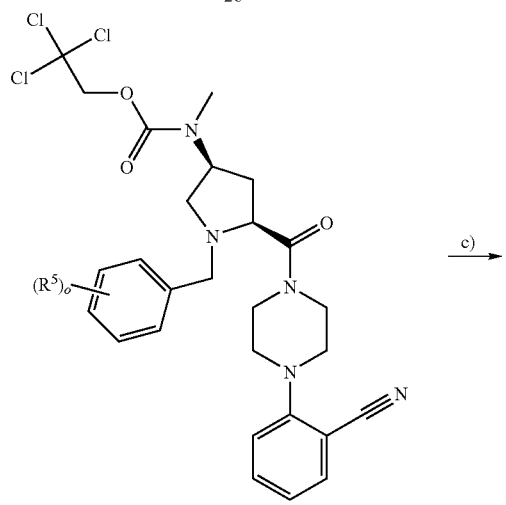

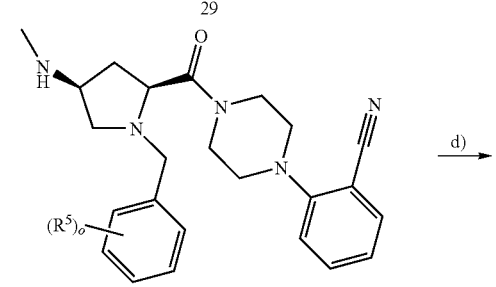

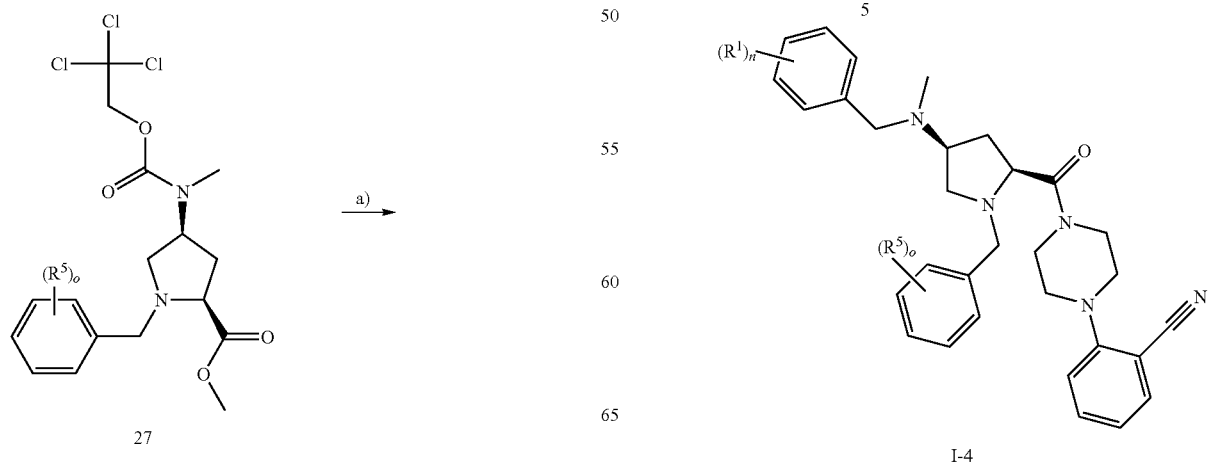

a) To a solution of (2S,4S)-1-benzyl-4-[methyl-(2,2,2-trichloro-ethoxycarbonyl)-amino]-pyrrolidine-2-carboxylic acid methyl ester in THF and methanol is added NaOH in water, and the reaction mixture is stirred overnight, and extracted with EA. The aqueous solution is acidified to ph 5-6 and extracted with EA. The organic phase is washed, dried and concentrated to give 1-benzyl-4-[methyl-(2,2,2-trichloro-ethoxycarbonyl)-amino]-pyrrolidine-2-carboxylic acid (28).

b) A mixture of 1-benzyl-4-[methyl-(2,2,2-trichloro-ethoxycarbonyl)-amino]-pyrrolidine-2-carboxylic acid, 2-piperazin-1-yl-benzonitrile, EDC and HOBT in $CH_2Cl_2$ is stirred for 5 min, then $Et_3N$ is added, and the reaction mixture is stirred at rt for about 12 h. After purification (1-benzyl-5-{1-[4-(2-cyano-phenyl)-piperazin-1-yl]-carbonyll}-pyrrolidin-3-yl)-methyl-carbamic acid 2,2,2-trichloro-ethyl ester (29) is obtained.

c) To a mixture of (1-benzyl-5-{1-[4-(2-cyano-phenyl)-piperazin-1-yl]-carbonyll}-pyrrolidin-3-yl)-methyl-carbamic acid 2,2,2-trichloro-ethyl ester and Zn in $CH_2Cl_2$ is added 5 drop of AcOH, and the mixture is stirred for about 2 h. After removal of the Zn power, the product is purified to afford 2-[4-(1-benzyl-4-methylamino-pyrrolidine-2-carbonyl)-piperazin-1-yl]-benzonitrile (5).

d) To a mixture of 2-[4-(1-benzyl-4-methylamino-pyrrolidine-2-carbonyl)-piperazin-1-yl]-benzonitrile and a corresponding benzaldehyde in $CH_2Cl_2$ and stirring at rt, it is added $NaBH(OAc)_3$ and $NEt_3$, and then the resulting mixture is stirred overnight. After purification 2-(4-{1-benzyl-4-[(3,4-dichloro-benzyl)-methyl-amino]-pyrrolidine-2-carbonyl}-piperazin-1-yl)-benzonitrile is obtained (I-4).

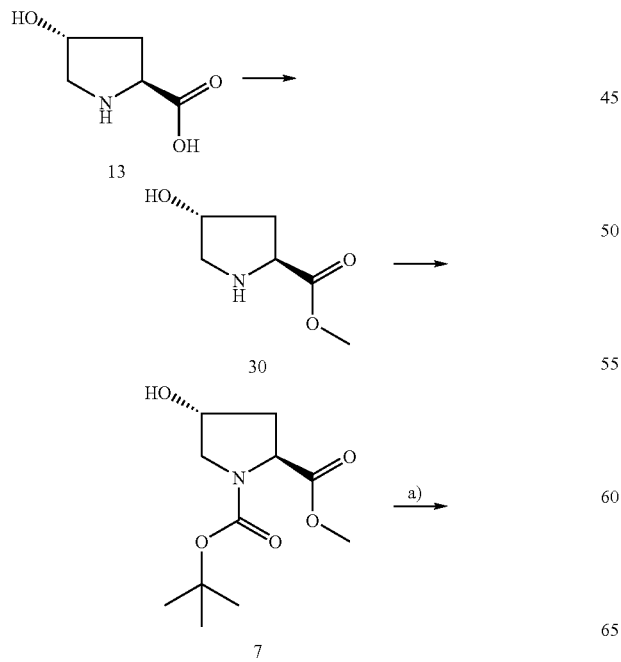

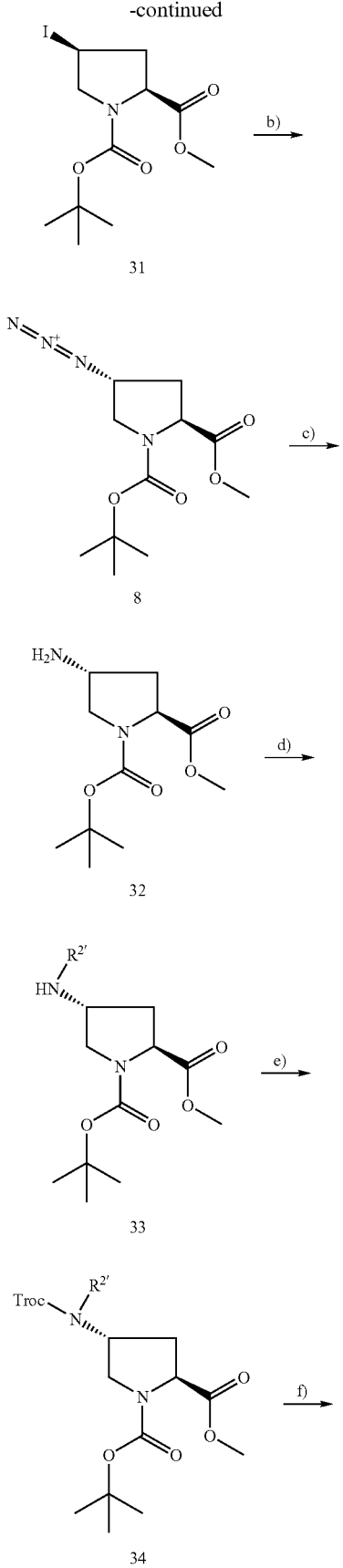

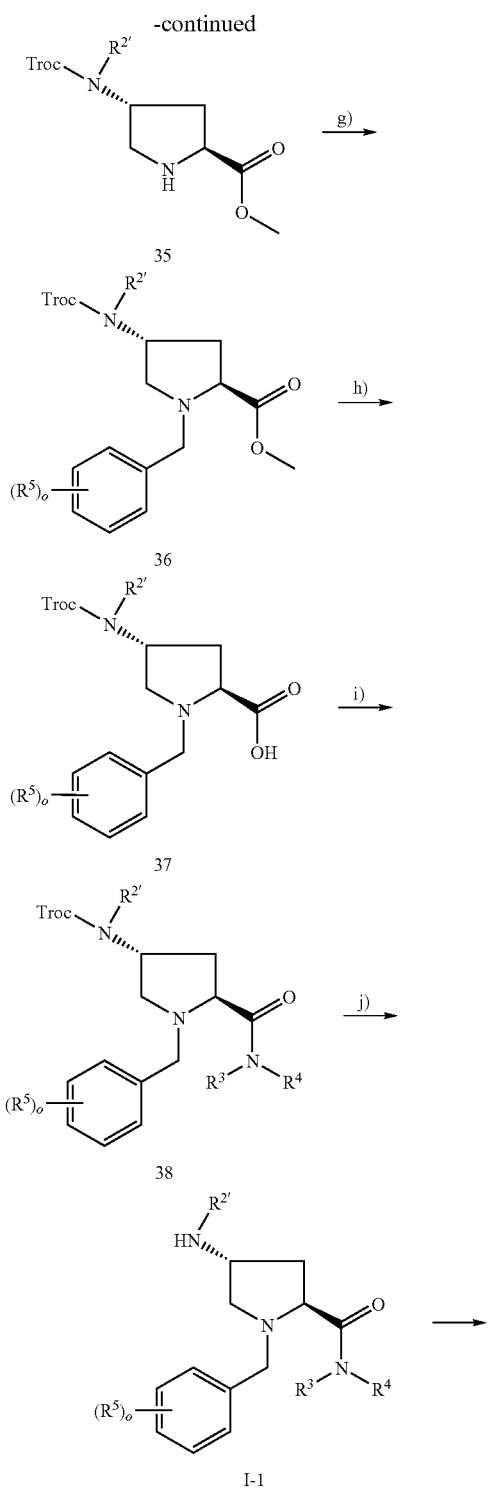

wherein R² is —CH₂-phenyl, substituted by (R¹)ₙ.

a) To a round-bottom flask equipped with a magnetic stir bar and an addition funnel under N₂ is added N-Boc-L-trans-4-hydroxy-proline methyl ester, PPh₃ and anhydrous THF. The solution is cooled to 0 centigrade, DEAD in THF is added; followed by the addition of MeI. The reaction mixture is allowed to warm to ambient temperature and stirred for about 10 hours. The solvent is removed and the crude product is purified to afford 4-iodo-pyrrolidine-1,2-dicarboxylic acid 1-tert-butyl ester 2-methyl ester (31).

b) To a solution of 4-iodo-pyrrolidine-1,2-dicarboxylic acid 1-tert-butyl ester 2-methyl ester in DMF is added NaN₃, the resulting mixture is heated to about 65 centigrade and stirred overnight. The mixture is diluted, extracted and dried. After removal of solvent, the residue is purified to give 4-azido-pyrrolidine-1,2-dicarboxylic acid 1-tert-butyl ester 2-methyl (8).

c) A solution of 4-azido-pyrrolidine-1,2-dicarboxylic acid 1-tert-butyl ester 2-methyl ester, THF and PPh₃ and water is refluxed for about 6 hours and then concentrated. The residue is dissolved in Et₂O and treated with HCl. The aqueous layer is extracted, washed, dried and concentrated to afford 4-amino-pyrrolidine-1,2-dicarboxylic acid 1-tert-butyl ester 2-methyl ester (32).

d) To a solution of 4-amino-pyrrolidine-1,2-dicarboxylic acid 1-tert-butyl ester 2-methyl ester, dissolved in DCM and cooled to 0 centigrade is added a corresponding benzaldehyde, then NaBH(OAc)₃ and 5 drops of HOAc. The mixture is warmed to room temperature and stirred overnight. The mixture is diluted with DCM, washed with brine, and dried. After removal of solvent, the crude 4-(benzylamino)-pyrrolidine-1,2-dicarboxylic acid 1-tert-butyl ester 2-methyl ester is obtained (33) and used for the next step without further purification.

e) To a solution of 4-(benzylamino)-pyrrolidine-1,2-dicarboxylic acid 1-tert-butyl ester 2-methyl ester in DCM, cooled to 0 centigrade it is added TrocCl, followed by Et₃N. The mixture is stirred overnight at room temperature and concentrated. The residue was purified to give 4-[(benzyl)-troc-amino]-pyrrolidine-1,2-dicarboxylic acid 1-tert-butyl ester 2-methyl ester (34).

f) To a solution of 4-[(2,4-difluoro-benzyl)-troc-amino]-pyrrolidine-1,2-dicarboxylic acid 1-tert-butyl ester 2-methyl ester in DCM, cooled to 0 centigrade it is added TFA. The mixture is stirred for 30 minutes, washed and dried. The organic layer is concentrated to give the crude 4-[(benzyl)-troc-amino]-pyrrolidine methyl ester (35).

g) To a solution of 4-[(2,4-difluoro-benzyl)-troc-amino]-pyrrolidine methyl ester in DCM, cooled to 0 centigrade, it is added a corresponding benzaldehyde, NaBH(OAc)₃ and 5 drops of HOAc. The resulting mixture is warmed to room temperature and stirred overnight. The reaction solution is washed with brine, dried and concentrated to give the crude 1-benzyl-4-[(benzyl)-troc-amino]-pyrrolidine methyl ester (36).

h) To a solution of 1-benzyl-4-[(benzyl)-troc-amino]-pyrrolidine methyl ester in methanol is added LiOH. The mixture is stirred overnight, acidified to PH=5, and extracted with DCM. The organic layer is dried and concentrated to give the crude 1-benzyl-4-[(benzyl)-troc-amino]-pyrrolidine carboxylic acid (37).

A mixture of 1-benzyl-4-[(benzyl)-troc-amino]-pyrrolidine carboxylic acid, EDCI, HOBT, Et₃N and a corresponding phenylpiperazine in DCM is stirred at room temperature overnight. Concentration of the mixture give the crude 1-benzyl-[4-(benzyl)-troc-amino]-pyrrolidin-2-yl}-[4-(phenyl)-piperazin-1-yl]-methanone (38).

i) To a solution of {1-benzyl-[4-(2,4-difluoro-benzyl)-troc-amino]-pyrrolidin-2-yl}-[4-(2-methoxy-phenyl)-piperazin-1-yl]-methanone in MeOH is added Zn dust and 5 drops of HOAc, and the mixture is refluxed overnight. The final compound of formula I-1 is obtained.

Scheme 7

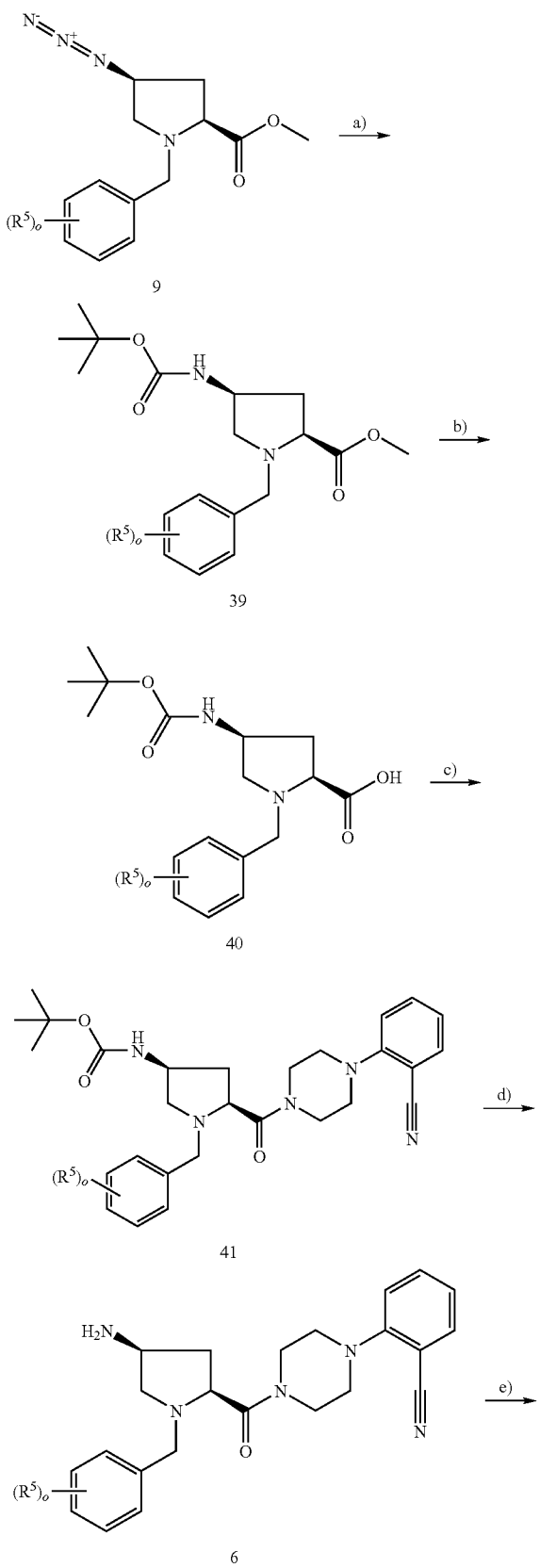

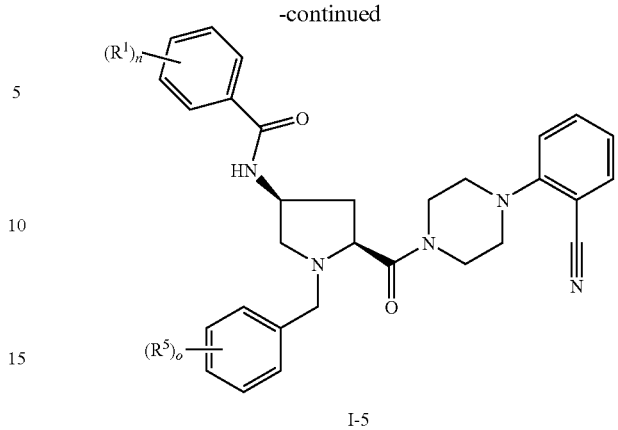

a) To a solution of 4-azido-1-benzyl-pyrrolidine-2-carboxylic acid methyl ester in THF is added triphenylphosphine and water under N2. The mixture is refluxed with stirring for about 6 h. After removal of the solvent, the residue is dissolved in $Et_2O$, treated with HCl, stirred for another 5 min. The solution is extracted with $Et_2O$, then the aqueous layer is neutralized with $NaHCO_3$ until PH>10, and extracted with DCM. The solvent is removed, then dissolved in $H_2O$, treated with $(Boc)_2O$ and stirred overnight. The product is then extracted into EA, which is washed with water and brine, dried, and concentrated to afford the title product 1-benzyl-4-tert-butoxycarbonylamino-pyrrolidine-2-carboxylic acid methyl ester (39).

b) 1-Benzyl-4-tert-butoxycarbonylamino-pyrrolidine-2-carboxylic methyl ester and LiOH are dissolved in $THF/H_2O$, and the resulting mixture is stirred for about 5 hours at room temperature. After removal of the solvent, the PH is adjusted to 6-7. The solid is collected and dried to afford 1-benzyl-4-tert-butoxycarbonylamino-pyrrolidine-2-carboxylic acid (40).

c) The mixture of 1-benzyl-4-tert-butoxycarbonylamino-pyrrolidine-2-carboxylic acid, 1-ethyl-3-(3-dimethylaminopropyl)-carbodiimidehydrochloride, N-hydroxybenzotriazole, 2-piperazin-1-yl-benzonitrile and triethylamine in DCM is stirred overnight. The crude product is purified to afford {1-benzyl-5-[4-(2-cyano-phenyl)-piperazine-1-carbonyl]-pyrrolidine-3-yl}carbamic acid tert-butyl ester (41).

d) {1-Benzyl-5-[4-(2-cyano-phenyl)-piperazine-1-carbonyl]-pyrrolidine-3-yl}carbamic acid tert-butyl ester is dissolved in $DCM/CF_3COOH$ and stirred overnight. After removal of solvent, the residue is treated with $NaHCO_3$ and extracted. The organic layer is dried and concentrated to afforded 2-[4-(4-amino-1-benzyl-pyrrolidine-2-carbonyl)-piperazin-1-yl]-benzonitrile (6).

e) To a mixture of 2-[4-(4-amino-1-benzyl-pyrrolidine-2-carbonyl)-piperazin-1-yl]-benzonitrile and a corresponding benzoyl chloride in DCM, triethylamine is added, and the resulting mixture is stirred overnight and then concentrated. The residue is purified to afford the compound of formula I-5.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

Abbreviations
DCM=dichloromethane;
DMF=N,N-dimethylformamide;
HPLC=high-performance liquid chromatography;
MS=mass spectroscopy;
THF=tetrahydrofurane;
EA=ethyl acetate
EDC=1-(3-dimethylaminopropyl)-3-ethylcarbodiimide
TEA triethylamine
TEMPO=2,2,6,6-tetramethyl-1-piperidine 1-oxyl
HOBT=1-hydroxybenzotriazole hydrate
DEAD=diethyl azodicarboxylate
TrocCl=2,2,2-trichloroethoxy carbonyl chloride
TFA=trifluoroacetic acid
EDCI=1-(3-dimethylaminopropyl)-3-ethylcarbodiimide As mentioned earlier, the compounds of formula I and their pharmaceutically usable addition salts possess valuable pharmacological properties. It has been found that the compounds of the present invention are antagonists of neurokinin 3 (NK-3) receptors. The compounds were investigated in accordance with the tests given hereinafter.

Experimental Procedure

The compounds were investigated in accordance with the tests given hereinafter.

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

Some results of preferred compounds with a good hNK-3 receptor affinity were shown in the following table 1.

TABLE 1

| Example | Data [µM] |
|---------|-----------|
| 1 | 0.0122 |
| 5 | 0.0376 |
| 7 | 0.063 |
| 8 | 0.0648 |
| 10 | 0.0567 |
| 12 | 0.0235 |
| 13 | 0.0394 |
| 32 | 0.0644 |
| 34 | 0.044 |
| 36 | 0.0948 |
| 38 | 0.058 |
| 40 | 0.071 |
| 45 | 0.0279 |
| 48 | 0.029 |
| 49 | 0.048 |
| 54 | 0.047 |
| 62 | 0.039 |
| 68 | 0.0412 |
| 87 | 0.052 |
| 88 | 0.097 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

EXAMPLE A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch firstly can be mixed in a mixer and then in a comminuting machine. The mixture then can be returned to the mixer; the talc can be added thereto and mixed thoroughly. The mixture then can be filled by machine into hard gelatin capsules.

EXAMPLE C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool, the suppositories then can be removed from the moulds and packed individually in wax paper or metal foil.

The following Examples illustrate the present invention without limiting it. All temperatures are given in degrees Celsius.

EXAMPLE 1

2-{4-[(2S,4S)-1-Benzyl-4-(2,4-difluoro-benzylamino)-pyrrolidine-2-carbonyl]-piperazin-1-yl}-benzonitrile a) 4-Azido-pyrrolidine-1,2-dicarboxylic acid 1-tert-butyl ester 2-methyl ester To a solution of trans-N-Boc-4-hydroxy-L-proline methyl ester (45 g, 0.183 mol) in pyridine (140 ml) and dry DCM (140 ml) at 0° C. was added dropwise 4-methyl-benzenesulfonyl chloride (41.9 g, 0.22 mol). After adding, the mixture was refluxed overnight. The solvent was evaporated and then the residue was dissolved in $CH_2Cl_2$ (140 ml). The organic phase was washed with water (150 ml), brine (140 mL), and dried over sodium sulphate. After removal of solvent, the crude 4-(toluene-4-sulfonyloxy)-pyrrolidine-1,2-dicarboxylic acid 1-tert-butyl ester 2-methyl ester 73.2 g (92%) was obtained as yellow oil, which was used in the following reaction without further purification.

To a solution of 4-(toluene-4-sulfonyloxy)-pyrrolidine-1,2-dicarboxylic acid 1-tert-butyl ester 2-methyl ester (30 g, 75 mmol) thus obtained above in dry DMF (150 ml) was added $NaN_3$ (9.5 g, 146.2 mmol) in one portion, and the reaction mixture was stirred at 50° C. for 5 h. The resulting mixture was diluted with ethyl acetate, washed with water (2×100 ml) and brine (100 ml), dried over anhydrous $MgSO_4$. After removal of solvent, the desired product 17.27 g (85%) 4-azido-pyrrolidine-1,2-dicarboxylic acid 1-tert-butyl ester 2-methyl ester was obtained as yellow oil. MS m/e=271.3 $[M+H]^+$.

b) 4-Azido-1-benzyl-pyrrolidine-2-carboxylic acid methyl ester

A mixture of 4-azido-pyrrolidine-1,2-dicarboxylic acid 1-tert-butyl ester 2-methyl ester (10.0 g, 36 mmol) in $CF_3COOH/CH_2Cl_2$=1:5 (50 ml) was stirred overnight at room temperature, and then concentrated to afford product 6.29 g (100%) as brown oil. To a solution of the brown oil (6.29.9 g, 37 mmol) in DCM (12 ml) was added benzaldehyde (5.87 g, 55.4 mmol), acetic acid (2.75 g, 46.25 mmol) and $NaBH(OAc)_3$ (15.68 g, 74 mmol). After stirred overnight, the reaction mixture was diluted with DCM, washed with aq. $NaHCO_3$, dried ($Na_2SO_4$) and concentrated. The residue was purified by flash column chromatography (EtOAc:PE=1:25) to afford the title product 4-azido-1-benzyl-pyrrolidine-2-carboxylic acid methyl ester 6.73 g (70%) as an colorless oil MS m/e=261.4 $[M+H]^+$.

c) 4-Amino-1-benzyl-pyrrolidine-2-carboxylic acid methyl ester

To a solution of 4-azido-1-benzyl-pyrrolidine-2-carboxylic acid methyl ester (6 g, 23 mmol) in THF (100 ml) under $N_2$ was added triphenylphosphine (12.08 g, 46 mmol) and water (1.036 mL, 57.56 mmol). The mixture was refluxed with stirring for 6 h. After removal of THF, the residue was dissolved in $Et_2O$, treated with 0.15N aqueous HCl, stirred for 5 min, and extracted with $Et_2O$ (2×150 ml). The aqueous solution was then treated with 10% $NaHCO_3$ until PH>10, and extracted by DCM (2×100 ml). The combined organic phases were dried over anhydrous $NaSO_4$, concentrated to afford product 4-amino-1-benzyl-pyrrolidine-2-carboxylic acid methyl ester 4.6 g (85%) as colorless oil. MS m/e=235.3 $[M+H]^+$.

d) 1-Benzyl-4-[tert-butoxycarbonyl-(2,4-difluoro-benzyl)-amino]-pyrrolidine-2-carboxylic acid methyl ester To a solution of 4-amino-1-benzyl-pyrrolidine-2-carboxylic acid methyl ester (2.89 g, 12.33 mmol) and 2,4-difluorobenzaldehyde (1.64 g, 11.52 mmol) in DCM (25 ml) were added $MgSO_4$ (8.1 g), AcOH (0.5 ml), and then $NaBH_3CN$ (1.09 g, 17.28 mmol). The reaction mixture was stirred overnight, and then diluted with DCM. The organic solution was washed with aq. $NaHCO_3$, dried ($Na_2SO_4$) and concentrated. The residue was dissolved in water, treated with $(Boc)_2O$ (1.09 g, 5 mmol), and then stirred overnight. The reaction mixture was extracted with DCM, dried, and concentrated to give product 1-benzyl-4-[tert-butoxycarbonyl-(2,4-difluoro-benzyl)-amino]-pyrrolidine-2-carboxylic acid methyl ester as white solid 1.9 g (36%). MS m/e=461.3 $[M+H]^+$.

e) 1-Benzyl-4-[tert-butoxycarbonyl-(2,4-difluoro-benzyl)-amino]-pyrrolidine-2-carboxylic acid To a solution of 1-benzyl-4-[tert-butoxycarbonyl-(2,4-difluoro-benzyl)-amino]-pyrrolidine-2-carboxylic acid methyl ester (109 g, 4.13 mmol) in $CH_3OH$ (10 ml) was added LiOH (0.826 g, 20.65 mmol), and the solution was stirred overnight at rt. After removal of solvent, the residue was dissolved in water, acidified until PH=5, and then extracted by EA. The organic phase was washed with water (2×50 mL) and brine (40 mL), dried over anhydrous $Na_2SO_4$, and concentrated to afford the product 1-benzyl-4-[tert-butoxycarbonyl-(2,4-difluoro-benzyl)-amino]-pyrrolidine-2-carboxylic acid 1.72 g (93%) as white solid. MS m/e=447.4 $[M+H]^+$.

f) 2-{4-[1-benzyl-4-(2,4-difluoro-benzylamino)-pyrrolidine-carbonyl]-piperazin-1-yl}-benzonitrile The mixture of 1-benzyl-4-[tert-butoxycarbonyl-(2,4-difluoro-benzyl)-amino]-pyrrolidine-2-carboxylic acid (60.0 mg, 0.134 mmol), 1-ethyl-3-(3-dimethylaminopropyl)-carbodiimide hydrochloride (50.0 mg, 0.268 mmol), N-hydroxybenzotriazole (19.0 mg, 0.134 mmol), and 2-piperazin-1-yl-benzonitrile (46.7 mg, 0.25 mmol), triethylamine (0.05 ml) in dry dichloromethane (2 ml) was stirred overnight at rt, and then treated with trifluoroacetic acid (1 mL). The resulting mixture was stirred at room temperature for another 5 h and concentrated. The residue was purified by preparative HPLC on reversed phase eluting with an acetonitrile/water [0.1% aq $NH_3$ (25%)] gradient to afford the title compound (6.7 mg, 9.7%) as a light yellow oil. MS m/e=516.4 $[M+H]^+$.

EXAMPLE 2

[(2S,4S)-1-Benzyl-4-(2,4-difluoro-benzylamino)-pyrrolidin-2-yl]-[4-(2-methoxy-ethyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(2-methyoxy-ethyl)-piperazine instead of 2-piperazin-1-yl-benzonitrile, to the title compound (5.7 mg, 8.9%) as light yellow oil. MS m/e=473.4 $[M+H]^+$.

EXAMPLE 3

[(2S,4S)-1-Benzyl-4-(2,4-difluoro-benzylamino)-pyrrolidin-2-yl]-(4-isopropyl-piperazin-1-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-isopropyl-piperazine instead of 2-piperazin-1-yl-benzonitrile, to the title compound (6.2 mg, 9.3%) as light yellow oil. MS m/e=457.4 $[M+H]^+$.

EXAMPLE 4

[(2S,4S)-1-Benzyl-4-(2,4-difluoro-benzylamino)-pyrrolidin-2-yl]-[4-(3-trifluoromethyl-pyridin-2-yl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3-trifluoromethyl-pyridin-2-yl)-piperazine instead of 2-piperazin-1-yl-benzonitrile, to the title compound (5.7 mg, 7.5%) as light yellow oil. MS m/e=560.4 $[M+H]^+$.

EXAMPLE 5

[(2S,4S)-1-Benzyl-4-(2,4-difluoro-benzylamino)-pyrrolidin-2-yl]-[4-(3-trifluoromethyl-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3-trifluoromethyl-phenyl)piperazine instead of 2-piperazin-1-yl-benzonitrile, to the title compound (8.2 mg, 11%) as light yellow oil. MS m/e=559.4 $[M+H]^+$.

EXAMPLE 6

1-(4-{4-[(2S,4S)-1-Benzyl-4-(2,4-difluoro-benzylamino)-pyrrolidine-2-carbonyl]-piperazin-1-yl}-phenyl)-ethanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(4-piperazine-1-yl-phenyl)-ethanone instead of 2-piperazin-1-yl-benzonitrile, to the title compound (5.8 mg, 8.1%) as light yellow oil. MS m/e=559.4 $[M+H]^+$.

EXAMPLE 7

[(2S,4S)-1-Benzyl-4-(2,4-difluoro-benzylamino)-pyrrolidin-2-yl]-(4-phenyl-piperazin-1-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-phenyl-piperazine instead of 2-piperazin-1-yl-benzonitrile, to the title compound (6.3 mg, 9.5%) as light yellow oil. MS m/e=491.4 $[M+H]^+$.

EXAMPLE 8

[(2S,4S)-1-Benzyl-4-(2,4-difluoro-benzylamino)-pyrrolidin-2-yl]-[4-(4-fluoro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(4-fluoro-phenyl)-piperazine instead of 2-piperazin-1-yl-benzonitrile, to the title compound (7.6 mg, II %) as light yellow oil. MS m/e=509.4 [M+H]$^+$.

EXAMPLE 9

[(2S,4S)-1-Benzyl-4-(2,4-difluoro-benzylamino)-pyrrolidin-2-yl]-[4-(3,4-dichloro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3,4-dichloro-phenyl)-piperazine instead of 2-piperazin-1-yl-benzonitrile, to the title compound (5.5 mg, 7.0%) as light yellow oil. MS m/e=559.4 [M+H]$^+$.

EXAMPLE 10

[(2S,4S)-1-Benzyl-4-(2,4-difluoro-benzylamino)-pyrrolidin-2-yl]-[4-(2-chloro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(2-chloro-phenyl)-piperazine instead of 2-piperazin-1-yl-benzonitrile, to the title compound (8.2 mg, 12%) as light yellow oil. MS m/e=525.4 [M+H]$^+$.

EXAMPLE 11

[(2S,4S)-1-Benzyl-4-(2,4-difluoro-benzylamino)-pyrrolidin-2-yl]-[4-(2-fluoro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(2-fluoro-phenyl)-piperazine instead of 2-piperazin-1-yl-benzonitrile, to the title compound (6.8 mg, 9.9%) as light yellow oil. MS m/e=509.4 [M+H]$^+$.

EXAMPLE 12

[(2S,4S)-1-Benzyl-4-(2,4-difluoro-benzylamino)-pyrrolidin-2-yl]-[4-(2-methoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(2-methoxy-phenyl)-piperazine instead of 2-piperazin-1-yl-benzonitrile, to the title compound (6.1 mg, 8.7%) as light yellow oil. MS m/e=521.4 [M+H]$^+$.

EXAMPLE 13

[(2S,4S)-1-Benzyl-4-(2,4-difluoro-benzylamino)-pyrrolidin-2-yl]-(6,7-dimethoxy-3,4-dihydro-1H-isoquinolin-2-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 6,7-dimethoxy-1,2,3,4-tetrahydro-isoquinoline instead of 2-piperazin-1-yl-benzonitrile, to the title compound (3.5 mg, 5.0%) as light yellow oil. MS m/e=522.4 [M+H]$^+$.

EXAMPLE 14

[(2S,4S)-1-Benzyl-4-(2,4-difluoro-benzylamino)-pyrrolidin-2-yl]-(4-phenyl-piperidin-1-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 4-phenyl-piperidine instead of 2-piperazin-1-yl-benzonitrile, to the title compound (12.5 mg, 8.3%) as light yellow oil. MS m/e=490.5 [M+H]$^+$.

EXAMPLE 15

[(2S,4S)-1-Benzyl-4-(2,4-difluoro-benzylamino)-pyrrolidin-2-yl]-[4-(3-chloro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3-chloro-phenyl)-piperazine instead of 2-piperazin-1-yl-benzonitrile, to the title compound (5.6 mg, 7.9%) as light yellow oil. MS m/e=525.4 [M+H]$^+$.

EXAMPLE 16

[(2S,4S)-1-Benzyl-4-(2,4-difluoro-benzylamino)-pyrrolidin-2-yl]-[4-(1,2-dihydro-1-methylsulfonyl-spiroindole-3-yl)-piperidin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1,2-dihydro-1-(methylsulfonyl)spiro[3H-indole-3,4'-piperidine] instead of 2-piperazin-1-yl-benzonitrile, to the title compound (12.4 mg, 15.5%) as light yellow oil. MS m/e=594.4 [M+H]$^+$.

EXAMPLE 17

[(2S,4S)-1-Benzyl-4-(2,4-difluoro-benzylamino)-pyrrolidin-2-yl]-[4-(5-chloro-2-methoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(5-chloro-2-methoxy-phenyl)-piperazine instead of 2-piperazin-1-yl-benzonitrile, to the title compound (2.6 mg, 3.5%) as light yellow oil. MS m/e=555.4 [M+H]$^+$.

EXAMPLE 18

[(2S,4S)-1-Benzyl-4-(2,4-difluoro-benzylamino)-pyrrolidin-2-yl]-[4-(3,5-dimethoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3,5-dimethoxy-phenyl)-piperazine instead of 2-piperazin-1-yl-benzonitrile, to the title compound (2.3 mg, 3.1%) as light yellow oil. MS m/e=551.5 [M+H]$^+$.

EXAMPLE 19

[(2S,4S)-1-Benzyl-4-(2,4-difluoro-benzylamino)-pyrrolidin-2-yl]-[4-(2,3-dichloro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(2,3-dichloro-phenyl)-piperazine instead of 2-piperazin-1-yl-benzonitrile, to the title compound (1.4 mg, 1.8%) as light yellow oil. MS m/e=559.4 [M+H]$^+$.

EXAMPLE 20

[(2S,4S)-1-Benzyl-4-(2,4-difluoro-benzylamino)-pyrrolidin-2-yl]-[4-(3,5-dichloro-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3,5-dichloro-phenyl)-piperazine instead of 2-piperazin-1-yl-benzonitrile, to the title compound (2.7 mg, 3.6%) as light yellow oil. MS m/e=559.4 [M+H]$^+$.

EXAMPLE 21

[(2S,4S)-1-Benzyl-4-(2,4-difluoro-benzylamino)-pyrrolidin-2-yl]-[4-(3-bromo-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3-bromo-phenyl)-piperazine instead of 2-piperazin-1-yl-benzonitrile, to the title compound (12.6 mg, 16%) as light yellow oil. MS m/e=569.3 [M+H]$^+$.

EXAMPLE 22

[(2S,4S)-1-Benzyl-4-(2,4-difluoro-benzylamino)-pyrrolidin-2-yl]-[4-(4-methoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(4-methoxy-phenyl)-piperazine instead of 2-piperazin-1-yl-benzonitrile, to the title compound (1.7 mg, 2.4%) as light yellow oil. MS m/e=521.4 [M+H]$^+$.

EXAMPLE 23

[(2S,4S)-1-Benzyl-4-(2,4-difluoro-benzylamino)-pyrrolidin-2-yl]-[4-(4-ethoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(4-ethoxy-phenyl)-piperazine instead of 2-piperazin-1-yl-benzonitrile, to the title compound (1.7 mg, 2.4%) as light yellow oil. MS m/e=535.5 [M+H]$^+$.

EXAMPLE 24

[(2S,4S)-1-Benzyl-4-(2,4-difluoro-benzylamino)-pyrrolidin-2-yl]-(4-p-tolyl-piperazin-1-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-p-tolyl-piperazine instead of 2-piperazin-1-yl-benzonitrile, to the title compound (1.8 mg, 2.6%) as light yellow oil. MS m/e=505.4 [M+H]$^+$.

EXAMPLE 25

[(2S,4S)-1-Benzyl-4-(2,4-difluoro-benzylamino)-pyrrolidin-2-yl]-[4-(3,4-dimethyl-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3,4-dimethyl-phenyl)-piperazine instead of 2-piperazin-1-yl-benzonitrile, to the title compound (9.7 mg, 14%) as light yellow oil. MS m/e=519.4 [M+H]$^+$.

EXAMPLE 26

4-{4-[(2S,4S)-1-Benzyl-4-(2,4-difluoro-benzylamino)-pyrrolidine-2-carbonyl]-piperazin-1-yl}-benzonitrile As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 4-piperazine-1-yl benzonitrile instead of 2-piperazin-1-yl-benzonitrile, to the title compound (11.8 mg, 17%) as light yellow oil. MS m/e=516.5 [M+H]$^+$.

EXAMPLE 27

[(2S,4S)-1-Benzyl-4-(2,4-difluoro-benzylamino)-pyrrolidin-2-yl]-[4-(3-methoxy-phenyl)-piperazin-1-yl]-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 1-(3-methoxy-phenyl)-piperazine instead of 2-piperazin-1-yl-benzonitrile, to the title compound (12.3 mg, 17.6%) as light yellow oil. MS m/e=521.4 [M+H]$^+$.

EXAMPLE 28

[(2S,4S)-1-Benzyl-4-(2,4-difluoro-benzylamino)-pyrrolidin-2-yl]-(4-methyl-piperidin-1-yl)-methanone As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using 4-methyl-piperidine instead of 2-piperazin-1-yl-benzonitrile, to the title compound (12.5 mg, 24%) as light yellow oil. MS m/e=428.5 [M+H]$^+$.

EXAMPLE 29

[(2S,4S)-1-Benzyl-4-(2,4-difluoro-benzylamino)-pyrrolidine-2-carbonyl]-piperidine-3-carboxylic acid ethyl ester As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using piperidine-3-carboxylic acid ethyl ester instead of 2-piperazin-1-yl-benzonitrile, to the title product [(2S,4S)-1-benzyl-4-(2,4-difluoro-benzylamino)-pyrrolidine-2-carbonyl]-piperidine-3-carboxylic acid ethyl ester (9.7 mg, 16% yield) as colorless oil. MS m/e=486.6 [M+H]$^+$.

EXAMPLE 30

[(2S,4S)-1-Benzyl-4-(2,4-difluoro-benzylamino)-pyrrolidine-2-carbonyl]-piperidine-4-carboxylic acid ethyl ester As described for Example 1f, 1-benzyl-4-[tert-butoxycarbonyl-(2,4-difluoro-benzyl)-amino]-pyrrolidine-2-carboxylic acid (60.0 mg, 0.134 mmol) was converted, using piperidine-4-carboxylic acid ethyl ester instead of 2-piperazin-1-yl-benzonitrile, to the title product [(2S,4S)-1-benzyl-4-(2,4-difluoro-benzylamino)-pyrrolidine-2-carbonyl]-piperidine-3-carboxylic acid ethyl ester (8.7 mg, 14% yield) as colorless oil. MS m/e=486.6 [M+H]$^+$.

EXAMPLE 31

2-{4-[(2S,4S)-1-Benzyl-4-(3,5-bis-trifluoromethyl-benzylamino)-pyrrolidine-2-carbonyl]-piperazin-1-yl}-benzonitrile a) 4-hydroxy-pyrrolidine-1,2-dicarboxylic acid 1-tert-butyl ester A solution of L-hydroxyproline (10.0 g, 76.2 mmol) in 80 ml of 10% aq Na$_2$CO$_3$ was added dropwise to a solution of Boc-anhydride (15.8 g, 72.4 mmol) in 44 ml of 10:1 THF/dioxane, and the mixture was stirred overnight. After removal of THF, the mixture was then washed with Et$_2$O, cooled to 0 degree, and acidified carefully to PH=2 with 3N HCl. The aqueous solution was extracted with EA and the organic layer was dried and concentrated to afford 4-hydroxy-pyrrolidine-1,2-dicarboxylic acid 1-tert-butyl ester, 12 g (68%) as yellow oil.

MS m/e=322.1 [M+H]$^+$.

b) 2-[4-(2-cyano-phenyl)-piperazie-1-carbonyl]-4-hydroxy-pyrrolidine-1-carboxylic acid tert-butyl ester The mixture of 4-hydroxy-pyrrolidine-1,2-dicarboxylic acid 1-tert-butyl ester (3.7 g, 0.016 mol), EDC.HCl (6.14 g, 0.32 mol), HOBT (2.16 g, 0.16 mol), 2-piperazin-1-yl-benzonitrile (3 g, 0.16 mmol) and Et$_3$N (4.85 ml) in dry DCM (50 ml) was stirred overnight. After removal of solvent, the residue was purified by column chromatography (EA:PE=1:1) to afford the product 2-[4-(2-cyano-phenyl)-piperazie-1-carbonyl]-4-hydroxy-pyrrolidine-1-carboxylic acid tert-butyl ester, 4 g (63%) as a white solid.
MS m/e=401.1 [M+H]$^+$.

c) 2-[4-(4-hydroxy-pyrrolidine-2-carbonyl)-piperazin-1-yl]-benzonitrile

2-[4-(2-Cyano-phenyl)-piperazie-1-carbonyl]-4-hydroxy-pyrrolidine-1-carboxylic acid tert-butyl ester was dissolved in 50 ml DCM/CF$_3$COOH (4:1), and stirred overnight. The solution was concentrated to afford product 2-[4-(4-hydroxy-pyrrolidine-2-carbonyl)-piperazin-1-yl]-benzonitrile, 2.1 g (100%) as a brown oil. MS m/e=301.1[M+H]$^+$.

d) 2-[4-(1-benzyl-4-pyrrolidine-2-carbonyl)-piperazin-41-yl]-benzonitrile

2-[4-(4-Hydroxy-pyrrolidine-2-carbonyl)-piperazin-1-yl]-benzonitrile (2.1 g, 7 mmol) was dissolved in DCM (20 mL), and then benzaldehyde (1.11 g, 10.5 mmol), and NaBH(OAc)$_3$ (2.95 g, 14 mmol) was added. After stirred overnight, the reaction mixture was diluted with DCM, washed with aq. NaHCO$_3$ (cautiously), dried (Na$_2$SO$_4$) and concentrated. The residue was purified by flash column chromatography to afford the title product 2-[4-(1-benzyl-4-pyrrolidine-2-carbonyl)-piperazin-41-yl]-benzonitrile as yellow oil in 1.8 g (67%). MS m/e=391.2 [M+H]$^+$.

e) 2-[4-(1-benzyl-4-oxo-pyrrolidine-2-carbonyl)-piperazin-41-yl]-benzonitrile

Oxalyl chloride (0.89 g, 7 mmol) was added dropwise to a solution of anhydrous DCM (50 mL) and DMSO (0.72 g, 9.2 mmol) at −78 degree. The reaction mixture was allowed to stirred for 30 min, then a solution of alcohol (1.8 g, 4.6 mmol) in DCM (50 mL) was added dropwise to keep the reaction temperature below −60 degree. Upon complete addition the reaction mixture was allowed to stir at −78 degree for 2 h; then triethylamine was added dropwise. After complete addition, the mixture was allowed to be warmed to RT, and stirred overnight. After water (10 mL) was added to the reaction mixture, the pH was adjusted to 10 with saturated NaHCO$_3$, and the product was extracted into DCM. Organic phase were combined, washed with brine, dried over K$_2$CO$_3$, and concentrated to afford product 2-[4-(1-benzyl-4-oxo-pyrrolidine-2-carbonyl)-piperazin-41-yl]-benzonitrile (1.5 g, 83%) as a brown oil. MS m/e=389.2 [M+H]$^+$.

f) 2-{4-[(2S,4S)-1-Benzyl-4-(3,5-bis-trifluoromethyl-benzylamino)-pyrrolidine-2-carbonyl]-piperazin-1-yl}-benzonitrile 2-[4-(1-Benzyl-4-oxo-pyrrolidine-2-carbonyl)-piperazin-41-yl]-benzonitrile (50 mg, 0.129 mmol) and 3,5-bis-trifluoromethyl-benzylamine (34.5 mg, 0.141 mmol) were dissolved in dry DCM (2 mL), then acetic acid (0.1 mL) and NaBH(OAc)$_3$ (27.3 mg, 0.258 mmol) was added. After stirred for 3 hours the reaction mixture was diluted with DCM, washed with aq. NaHCO$_3$, dried (Na$_2$SO$_4$) and concentrated. The residue was purified by Prep-LCMS to afford the title product 2-{4-[(2S,4S)-1-benzyl-4-(3,5-bis-trifluoromethyl-benzylamino)-pyrrolidine-2-carbonyl]-piperazin-1-yl}-benzonitrile, 7.8 mg (9%) as an oil.

MS m/e=616.4 [M+H]$^+$.

EXAMPLE 32

2-(4-{(2S,4S)-1-Benzyl-4-[(3,5-bis-trifluoromethyl-benzyl)-methyl-amino]-pyrrolidine-2-carbonyl}-piperazin-1-yl)-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using (3,5-bis-trifluoromethyl-benzyl)-methyl-amine instead of 3,5-bis-trifluoromethyl-benzylamine, to the title compound (10.9 mg, 12.3%) as light yellow oil. MS m/e=630.4 [M+H]$^+$.

EXAMPLE 33

2-(4-{(2S,4S)-1-Benzyl-4-[(2,4-difluoro-benzyl)-methyl-amino]-pyrrolidine-2-carbonyl}-piperazin-1-yl)-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using (2,4-difluoro-benzyl)-methyl-amine instead of 3,5-bis-trifluoromethyl-benzylamine, to the title compound (9.5 mg, 12.7%) as light yellow oil. MS m/e=530.4 [M+H]$^+$.

EXAMPLE 34

2-{4-[(2S,4S)-1-Benzyl-4-(3,5-dimethoxy-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3,5-dimethoxy-benzylamine instead of 3,5-bis-trifluoromethyl-benzylamine, to the title compound (14.3 mg, 18.8%) as light yellow oil. MS m/e=540.4 [M+H]$^+$.

EXAMPLE 35

2-{4-[(2S,4S)-1-Benzyl-4-(2-methoxy-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-methoxy-benzylamine instead of 3,5-bis-trifluoromethyl-benzylamine, to the title compound (6.7 mg, 9.3%) as light yellow oil. MS m/e=510.4 [M+H]$^+$.

EXAMPLE 36

2-{4-[(2S,4S)-1-Benzyl-4-(2-trifluoromethyl-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-trifluoromethyl-benzylamine instead of 3,5-bis-trifluoromethyl-benzylamine, to the title compound (11 mg, 14.2%) as light yellow oil. MS m/e=548.3 [M+H]$^+$.

EXAMPLE 37

2-{4-[(2S,4S)-1-Benzyl-4-(2,3-difluoro-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2,3-difluoro-benzylamine instead of 3,5-bis-trifluoromethyl-benzylamine, to the title compound (5.1 mg, 7%) as light yellow oil.

MS m/e=516.3 [M+H]$^+$.

EXAMPLE 38

2-{4-[(2S,4S)-1-Benzyl-4-(2-chloro-5-trifluoromethyl-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-chloro-5-trifluoromethyl-benzylamine instead of 3,5-bis-trifluoromethyl-benzylamine, to the title compound (5.5 mg, 6.7%) as light yellow oil. MS m/e=582.3 [M+H]$^+$.

EXAMPLE 39

2-{4-[(2S,4S)-1-Benzyl-4-(2-fluoro-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-fluoro-benzylamine instead of 3,5-bis-trifluoromethyl-benzylamine, to the title compound (2 mg, 2.8%) as light yellow oil. MS m/e=498.4 [M+H]$^+$.

EXAMPLE 40

2-{4-[(2S,4S)-1-Benzyl-4-(3-chloro-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3-chloro-benzylamine instead of 3,5-bis-trifluoromethyl-benzylamine, to the title compound (4.3 mg, 5.9%) as light yellow oil.

MS m/e=514.3[M+H]$^+$.

EXAMPLE 41

2-{4-[(2S,4S)-1-Benzyl-4-(4-trifluoromethoxy-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 4-trifluoromethoxy-benzylamine instead of 3,5-bis-trifluoromethyl-benzylamine, to the title compound (2.3 mg, 2.9%) as light yellow oil. MS m/e=564.4 [M+H]$^+$.

EXAMPLE 42

2-{4-[(2S,4S)-1-Benzyl-4-(3,5-dichloro-benzy-lamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3,5-dichloro-benzylamine instead of 3,5-bis-trifluoromethyl-benzylamine, to the title compound (9.5 mg, 12.3%) as light yellow oil. MS m/e=548.3 [M+H]$^+$.

EXAMPLE 43

2-{4-[(2S,4S)-1-Benzyl-4-(2-chloro-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-chloro-benzylamine instead of 3,5-bis-trifluoromethyl-benzylamine, to the title compound (10 mg, 13.8%) as light yellow oil.
MS m/e=548.3 [M+H]$^+$.

EXAMPLE 44

2-{4-[(2S,4S)-1-Benzyl-4-(2-bromo-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 2-bromo-benzylamine instead of 3,5-bis-trifluoromethyl-benzylamine, to the title compound (7.2 mg, 9.1%) as light yellow oil.
MS m/e=560.3 [M+H]$^+$.

EXAMPLE 45

2-{4-[(2S,4S)-1-Benzyl-4-(3-chloro-4-fluoro-benzy-lamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3-chloro-4-fluoro-benzylamine instead of 3,5-bis-trifluoromethyl-benzylamine, to the title compound (4.5 mg, 4.5%) as light yellow oil. MS m/e=532.5 [M+H]$^+$.

EXAMPLE 46

2-{4-[(2S,4S)-1-Benzyl-4-(3,4-difluoro-benzy-lamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3,4-difluoro-benzylamine instead of 3,5-bis-trifluoromethyl-benzylamine, to the title compound (2.2 mg, 3.0%) as light yellow oil.
MS m/e=516.4 [M+H]$^+$.

EXAMPLE 47

2-{4-[(2S,4S)-1-Benzyl-4-(4-fluoro-benzylamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 4-fluoro-benzylamine instead of 3,5-bis-trifluoromethyl-benzylamine, to the title compound (4.0 mg, 5.7%) as light yellow oil.
MS m/e=498.4 [M+H]$^+$.

EXAMPLE 48

2-{4-[(2S,4S)-1-Benzyl-4-(3,4-dichloro-benzy-lamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3,4-dichloro-benzylamine instead of 3,5-bis-trifluoromethyl-benzylamine, to the title compound (7.1 mg, 9.2%) as light yellow oil. MS m/e=548.3 [M+H]$^+$.

EXAMPLE 49

2-{4-[(2S,4S)-1-Benzyl-4-(3-chloro-2-fluoro-benzy-lamino)-pyrrolidine-2-carbonyl]-piperazin-1-yl}-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using 3-chloro-2-fluoro-benzylamine instead of 3,5-bis-trifluoromethyl-benzylamine, to the title compound (6.6 mg, 6.6%) as light yellow oil. MS m/e=532.4 [M+H]$^+$.

EXAMPLE 50

2-[4-((2S,4S)-1-Benzyl-4-benzylamino-pyrrolidine-2-carbonyl)-piperazin-1-yl]-benzonitrile As described for Example 31f, 2-[4-(1-benzyl-4-oxo-pyrrolidine-2-carbonyl)-piperazin-4-yl]-benzonitrile (50.0 mg, 0.129 mmol) was converted, using benzylamine in stead of 3,5-bis-trifluoromethyl-benzylamine, to the title compound (1.2 mg, 1.8%) as light yellow oil. MS m/e=480.4 [M+H]$^+$.

EXAMPLE 51

2-{4-[1-(2,3-Difluoro-benzyl)-4-(2,4-difluoro-ben-zylamino)-pyrrolidine-2-carbonyl]-piperazin-1-yl}-benzonitrile a) 4-[(2,4-Difluoro-benzyl)-(2,2,2-trichloro-ethoxy-carbonyl)-amino]-pyrrolidine-1,2-dicarboxylicacid 1-tert-butyl ester 2-methyl ester To a solution of 4-[(2,4-difluoro-benzylamino]-pyrrolidine-1,2-dicarboxylicacid 1-tert-butyl ester 2-methyl ester (7 g, 18.9 mmol) in dry DCM (100 ml) cooled to 0 degree was added TrocCl (6.02 g, 28.4 mmol) and TEA (5.22 ml, 37.8 mmol) dropwise. The mixture was stirred overnight, washed with Na$_2$CO$_3$, brine, dried over Na$_2$SO$_4$ and concentrated in vacuo. Purification by chromatography on silica gel (PE: EA=3:1) afforded the title product (8 g, 14.7 mmol) as yellow oil. MS m/e=545.2 [M+H]$^+$.

b) 4-[(2,4-Difluoro-benzyl)-(2,2,2-trichloro-ethoxy-carbonyl)-amino]-pyrrolidine-1,2-dicarboxylicacid 1-tert-butyl ester To a solution of 4-[(2,4-difluoro-benzyl)-(2,2,2-trichloro-ethoxycarbonyl)-amino]-pyrrolidine-1,2-dicarboxylicacid 1-tert-butyl ester 2-methyl ester (8 g, 14.7 mmol) in MeOH (50 ml) cooled to 0 degree was added LiOH (2.47 g, 58.8 mmol), and the mixture was stirred overnight. After removal of methanol, the residue was acidified with 2M HCl. The aqueous layer was extracted with EA, and the organic solution was dried and concentrated. The residue was purified by chromatography (PE:EA=3:1) on silica gel to afford the title product as yellow oil (3.5 g, 6.5 mmol). MS m/e=531.2 [M+H]$^+$.

c) 2-[4-(2-Cyano-phenyl)-piperazine-1-carbonyl]-4-[(2,4-difluoro-benzyl)-(2,2,2-trichloroethoxycarbonyl)-amino]-pyrrolidine-1-carboxylic acid tert-butyl ester To a solution of 4-[(2,4-difluoro-benzyl)-(2,2,2-trichloroethoxycarbonyl)-amino]-pyrrolidine-1,2-dicarboxylicacid 1-tert-butyl ester (3.5 g, 6.6 mmol), HOBt (1.4 g, 10 mmol), 1-(2-cyanophenyl)piperazine (1.5 g, 7.9 mmol) in DCM (50 ml) were added Et$_3$N (1.8 ml, 13.2 mmol) and EDC.HCl (1.9 g, 10 mmol). The mixture was stirred overnight, then washed with 10% citric acid, Na$_2$CO$_3$, brine, dried and concentrated to give the title product as a colorless oil (4.5 g, 6.4 mmol). MS m/e=700.3 [M+H]$^+$.

d) {5-[4-(2-Cyano-phenyl)-piperazine-1-carbonyl]-pyrrolidin-3-yl}-(2,4-difluoro-benzyl)-carbamic acid 2,2,2-trichloro-ethyl ester A mixture of 2-[4-(2-cyano-phenyl)-piperazine-1-carbonyl]-4-[(2,4-difluoro-benzyl)-(2,2,2-trichloroethoxycarbonyl)-amino]-pyrrolidine-1-carboxylic acid tert-butyl ester (4.5 g, 6.4 mmol) and CF$_3$COOH (3.65 g, 32 mmol) were stirred at rt. for 5 h, and then concentrated to give the crude product as dark yellow oil (3.5 g, 5.8 mmol).
MS m/e=600.2 [M+H]$^+$.

e) {1-(2,3-Difluoro-benzyl)-5-[4-(2-cyano-phenyl)-piperazine-1-carbonyl]-pyrrolidin-3-yl}-(2,4-difluoro-benzyl)-carbamic acid 2,2,2-trichloro-ethyl ester A mixture of {5-[4-(2-cyano-phenyl)-piperazine-1-carbonyl]-pyrrolidin-3-yl}-(2,4-difluoro-benzyl)-carbamic acid 2,2,2-trichloro-ethyl ester (0.078 g, 0.13 mmol), 2,3-difluorobenzaldehyde and acetic acid (cat.) in DCM (5 ml) was stirred for 20 min, and then NaBH(OAc)$_3$ (0.041 g, 0.13 mmol) was carefully added. The reaction mixture was stirred overnight, and was concentrated to give crude product which was directly used for next step.

f) 2-{4-[1-(2,3-Difluoro-benzyl)-4-(2,4-difluoro-benzylamino)-pyrrolidine-2-carbonyl]-piperazin-1-yl}-benzonitrile {1-(2,3-Difluoro-benzyl)-5-[4-(2-cyano-phenyl)-piperazine-1-carbonyl]-pyrrolidin-3-yl}-(2,4-difluoro-benzyl)-carbamic acid 2,2,2-trichloro-ethyl ester (0.13 mmol) and Zn (0.068 g, 1.04 mmol) was dissolved in MeOH (5 ml), and PH was adjust to 5-6 using acetic acid. The mixture was heated to reflux and stirred for 30 min. After removal of methanol, the residue was purified by HPLC to afford final product (5.5 mg, 0.01 mmol) as yellow oil in 8% yield. MS m/e=552.4 [M+H]$^+$.

EXAMPLE 52

2-{4-[4-(2,4-Difluoro-benzylamino)-1-(2-fluoro-benzyl)-pyrrolidine-2-carbonyl]-piperazin-1-yl}-benzonitrile As described for Example 51, using 2-fluorobenzaldehyde instead of 2,3-difluorobenzaldehyde, 2-{4-[4-(2,4-difluoro-benzylamino)-1-(2-fluoro-benzyl)-pyrrolidine-2-carbonyl] piperazin-1-yl}-benzonitrile was obtained in 23% yield as yellow oil. MS m/e=534.5 [M+H]$^+$.

EXAMPLE 53

2-{4-[1-(3-Chloro-benzyl)-4-(2,4-difluoro-benzylamino)-pyrrolidine-2-carbonyl]-piperazin-1-yl}-benzonitrile As described Example 51, using 3-chlorobenzaldehyde instead of 2,3-difluorobenzaldehyde, 2-{4-[1-(3-chloro-benzyl)-4-(2,4-difluoro-benzylamino)-pyrrolidine-2-carbonyl]-piperazin-1-yl}-benzonitrile was obtained in 12% yield as yellow oil. MS m/e=550.3 [M+H]$^+$.

EXAMPLE 54

2-{4-[4-(2,4-Difluoro-benzylamino)-1-(3-fluoro-benzyl)-pyrrolidine-2-carbonyl]-piperazin-lyl}-benzonitrile As described for Example 51, using 3-fluorobenzaldehyde instead of 2,3-difluorobenzaldehyde, 2-{4-[4-(2,4-difluoro-benzylamino)-1-(3-fluoro-benzyl)-pyrrolidine-2-carbonyl]-piperazin-lyl}-benzonitrile was obtained in 14% yield as yellow oil. MS m/e=534.3 [M+H]$^+$.

EXAMPLE 55

2-{4-[1-(2-Chloro-benzyl)-4-(2,4-difluoro-benzylamino)-pyrrolidine-2-carbonyl]-piperazin-1-yl}-benzonitrile As described for Example 51, using 2-chlorobenzaldehyde instead of 2,3-difluorobenzaldehyde, 2-{4-[1-(2-chloro-benzyl)-4-(2,4-difluoro-benzylamino)-pyrrolidine-2-carbonyl]-piperazin-1-yl}-benzonitrile was obtained in 9.8% yield as yellow oil. MS m/e=550.3 [M+H]$^+$.

EXAMPLE 56

[(2S,4S)-1-Benzyl-4-(3,5-bis-trifluoromethyl-benzylamino)-pyrrolidin-2-yl]-[4-(3-trifluoromethyl-phenyl)-piperazin-1-yl]-methanone a) 1-Benzyl-4-oxo-pyrrolidine-2-carboxylic acid methyl ester A solution of 1-benzyl-4-hydroxy-pyrrolidine-2-carboxylic acid methyl ester (12.13 g, 49.5 mmol) in 250 mL of DCM cooled at 0° C. was treated with trichloroisocyanuric acid (11.48 g, 49.5 mmol) and TEMPO (770 mg, 4.95 mmol), and then the reaction mixture was stirred at 0° C. for 1 h. The mixture was diluted with DCM and washed with saturated aqueous NaHCO$_3$, 1 M HCl, and brine. The organic layer was dried over Na$_2$SO$_4$ and concentrated to afford the product 1-benzyl-4-oxo-pyrrolidine-2-carboxylic acid methyl ester 11.5 g (96%) as a colorless oil. MS m/e=234.3 [M+H]$^+$.

b) 1-Benzyl-4-(3,5-bis-trifluoromethyl-benzylamino)-pyrrolidine-2-carboxylic acid methyl ester Benzyl-4-oxo-pyrrolidine-2-carboxylic acid methyl ester (100 mg, 0.428 mmol) and 3,5-bis-trifluoromethyl-benzylamine (125 mg, 0.514 mmol) were dissolved in dry DCM (2 mL), acetic acid (0.1 mL) and NaBH(OAc)$_3$ (180.6 mg, 0.856 mmol) was then added. After stirred for 3 hours the reaction mixture was diluted with DCM, washed with saturated NaHCO₃ (cautiously), dried (Na₂SO₄) and concentrated. The residue was purified by flash column chromatography to afford the title product 1-benzyl-4-(3,5-bis-trifluoromethyl-benzylamino)-pyrrolidine-2-carboxylic acid methyl ester 124 mg (63%) as a yellow oil.

MS m/e=461.2 [M+H]⁺.

c) 1-Benzyl-4-(3,5-bis-trifluoromethyl-benzylamino)-pyrrolidine-2-carboxylic acid Benzyl-4-(3,5-bis-trifluoromethyl-benzylamino)-pyrrolidine-2-carboxylic acid methyl ester (124 mg, 0.269 mmol) and LiOH (53.9 mg, 1.5 mmol) were dissolved in THF/H₂O (4 mL), and then stirred overnight. After removal of solvent, the residue was neutralized to PH=6-7, and then extracted by EA twice. The organic layer was washed with water and brine, dried, and concentrated to afford the title product 1-benzyl-4-(3,5-bis-trifluoromethyl-benzylamino)-pyrrolidine-2-carboxylic acid, 65 mg (54.2%) as a yellow solid. MS m/e=447.3 [M+H]⁺.

d) [(2S,4S)-1-Benzyl-4-(3,5-bis-trifluoromethyl-benzylamino)-pyrrolidin-2-yl]-[4-(3-trifluoromethyl-phenyl)-piperazin-1-yl]-methanone The mixture of 1-benzyl-4-(3,5-bis-trifluoromethyl-benzylamino)-pyrrolidine-2-carboxylic acid (65 mg, 0.146 mmol), 1-ethyl-3-(3-dimethylaminopropyl)-carbodiimide hydrochloride (54.5.0 mg, 0.292 mmol), N-hydroxybenzotriazole (20.7 mg, 0.146 mmol), and 1-(3-trifluoromethyl-phenyl)-piperazine (29.67 mg, 0.219 mmol), triethylamine (0.08 ml) in dry dichloromethane (2 mL) was stirred overnight, and then concentrated. The residue was purified by preparative HPLC on reversed phase eluting with an acetonitrile/water [0.1% aq NH₃ (25%)] gradient to afford the title compound (10.2 mg, 10.6%) as a light yellow oil. MS m/e=659.4 [M+H]⁺.

EXAMPLE 57

{(2S,4S)-1-Benzyl-4-[(3,5-bis-trifluoromethyl-benzyl)-methyl-amino]-pyrrolidin-2-yl}-[4-(2-methoxy-phenyl)-piperazin-1-yl]-methanone As described for Example 56b and 56d, 1-benzyl-4-oxo-pyrrolidine-2-carboxylic acid methyl ester (100 mg, 0.428 mmol) was converted, using (3,5-bis-trifluoromethyl-benzyl)-methyl-amine instead of 3,5-bis-trifluoromethyl-benzylamine, and using 1-(2-methoxy-phenyl)-piperazine instead of 1-(3-trifluoromethyl-phenyl)-piperazine, to the title compound (11.3 mg, 12.2%) as light yellow oil. MS m/e=635.5 [M+H]⁺.

EXAMPLE 58

{(2S,4S)-1-Benzyl-4-[(3,5-bis-trifluoromethyl-benzyl)-methyl-amino]-pyrrolidin-2-yl}-(4-m-tolyl-piperazin-1-yl)-methanone As described for Example 56b and 56d, 1-benzyl-4-oxo-pyrrolidine-2-carboxylic acid methyl ester (100 mg, 0.428 mmol) was converted, using (3,5-bis-trifluoromethyl-benzyl)-methyl-amine instead of 3,5-bis-trifluoromethyl-benzylamine, and using 1-m-tolyl-piperzine instead of 1-(3-trifluoromethyl-phenyl)-piperazine, to the title compound (12.1 mg, 13.4%) as light yellow oil. MS m/e=619.4[M+H]⁺.

EXAMPLE 59

4-[(2S,4S)-1-Benzyl-4-(3,5-bis-trifluoromethyl-benzylamino)-pyrrolidine-2-carbonyl]-piperazine-1-carboxylic acid ethyl ester As described for Example 56d, 1-benzyl-4-(3,5-bis-trifluoromethyl-benzylamino)-pyrrolidine-2-carboxylic acid (65 mg, 0.146 mmol) was converted, using piperazine-1-carboxylic acid ethyl ester instead of 1-(3-trifluoromethyl-phenyl)-piperazine, to the title compound (6.8 mg, 7.5%) as light yellow oil. MS m/e=587.3 [M+H]⁺.

EXAMPLE 60

[(2S,4S)-1-Benzyl-4-(3,5-bis-trifluoromethyl-benzylamino)-pyrrolidin-2-yl]-(4-m-tolyl-piperazin-1-yl)-methanone As described for Example 56d, 1-benzyl-4-(3,5-bis-trifluoromethyl-benzylamino)-pyrrolidine-2-carboxylic acid (65 mg, 0.146 mmol) was converted, using 1-m-tolyl-piperzine instead of 1-(3-trifluoromethyl-phenyl)-piperazine, to the title compound (7.5 mg, 8.5%) as light yellow oil. MS m/e=605.4 [M+H]⁺.

EXAMPLE 61

(4-Benzoyl-piperazin-1-yl)-[(2S,4S)-1-benzyl-4-(3,5-bis-trifluoromethyl-benzylamino)-pyrrolidin-2-yl]-methanone As described for Example 56d, 1-benzyl-4-(3,5-bis-trifluoromethyl-benzylamino)-pyrrolidine-2-carboxylic acid (65 mg, 0.146 mmol) was converted, using phenyl-piperazin-yl-methanone instead of 1-(3-trifluoromethyl-phenyl)-piperazine, to the title compound (10.9 mg, 12.1%) as light yellow oil. MS m/e=619.4 [M+H]⁺.

EXAMPLE 62

{(2S,4S)-1-Benzyl-4-[(3,5-bis-trifluoromethyl-benzyl)-methyl-amino]-pyrrolidin-2-yl}-[4-(3-trifluoromethyl-phenyl)-piperazin-1-yl]-methanone As described for Example 56b and 56d, 1-benzyl-4-oxo-pyrrolidine-2-carboxylic acid methyl ester (100 mg, 0.428 mmol) was converted, using (3,5-bis-trifluoromethyl-benzyl)-methyl-amine instead of 3,5-bis-trifluoromethyl-benzylamine, to the title compound (9.9 mg, 10.1%) as light yellow oil. MS m/e=673.4 [M+H]⁺.

EXAMPLE 63

{(2S,4S)-1-Benzyl-4-[(3,5-bis-trifluoromethyl-benzyl)-methyl-amino]-pyrrolidin-2-yl}-[4-(2-fluoro-phenyl)-piperazin-1-yl]-methanone As described for Example 56b and 56d, 1-benzyl-4-oxo-pyrrolidine-2-carboxylic acid methyl ester (100 mg, 0.428 mmol) was converted, using (3,5-bis-trifluoromethyl-benzyl)-methyl-amine instead of 3,5-bis-trifluoromethyl-benzylamine, and using 1-(2-fluoro-phenyl)-piperazine instead of 1-(3-trifluoromethyl-phenyl)-piperazine, to the title compound (5.5 mg, 6.0%) as light yellow oil. MS m/e=623.4 [M+H]$^+$.

EXAMPLE 64

8-{(2S,4S)-1-(3-Chloro-benzyl)-4-[(2,4-difluoro-benzyl)-methyl-amino]-pyrrolidine-2-carbonyl}-2-cyclohexyl-1,3,8-triaza-spiro[4.5]dec-1-en-4-one a) (2S,4R)-1-(3-Chloro-benzyl)-4-hydroxy-pyrrolidine-2-carboxylic acid methyl ester Chloro-3-chloromethyl-benzene (15.2 ml, 120 mmol) was added to the mixture of 4-hydroxy-pyrrolidine-2-carboxylic acid methyl ester hydrochloride (14.5 g, 80 mmol) and triethylamine (18.6 g, 180 mmol) in dichloromethane (120 ml). The reaction mixture was refluxed overnight. After cooling, 1M aqueous sodium hydroxide was added, and the mixture was extracted with dichloromethane. The extract was washed with brine, dried over sodium sulfate, concentrated and purified by chromatography on silica gel (hex/EA=5:1 to hex/EA=3:1) to give 14 g title product as yellow oil in 65% yield.
MS m/e=270.7 [M+H]$^+$.

b) (S)-1-(3-Chloro-benzyl)-4-oxo-pyrrolidine-2-carboxylic acid methyl ester

Oxalyl chloride (3.8 g, 30 mmol) was added dropwise to a solution of anhydrous CH$_2$Cl$_2$ (30 mL) and DMSO (3.13 g, 40 mmol) at −78° C. The reaction mixture was allowed to equilibrate for 10 min, after which time a solution of alcohol (5.4 g, 20 mmol) in CH$_2$Cl$_2$ (30 mL) was added dropwise at a rate to keep the reaction temperature below −60° C. Upon complete addition the reaction mixture was allowed to stir at −78° C. for 2 h; then triethylamine (60 mmol) was added dropwise. After complete addition, the reaction mixture was allowed to be warmed to room temperature. H$_2$O (50 mL) was added to the reaction mixture, the PH was adjusted to 10 with saturated aqueous NaHCO$_3$, and the product was extracted with DCM (3×20 mL). All organic phases were combined, washed with brine, dried over K$_2$CO$_3$, and concentrated in vacuo to yield crude product (5.4 g) in 100% yield. MS m/e=268.7 [M+H]$^+$.

c) (2S,4S)-1-(3-Chloro-benzyl)-4-[(2,4-difluoro-benzyl)-methyl-amino]-pyrrolidine-2-carboxylic acid methyl ester The ketone (0.803 g, 3 mmol), (2,4-difluoro-benzyl)-methyl-amine (0.71 g, 4.5 mmol) and acetic acid (cat.) was dissolved in DCM (20 ml) and the mixture was stirred for 20 min. After cooled to 0° C., NaBH(OAc)$_3$ (1.27 g, 6 mmol) was carefully added, then the mixture was warmed to r.t and stirred overnight. The solution was washed with aq. NaHCO$_3$, brine, dried and concentrated to afford the crude product as yellow oil (1.1 g) in 90% yield.
MS m/e=409.9 [M+H]$^+$.

d) (2S,4S)-1-(3-Chloro-benzyl)-4-[(2,4-difluoro-benzyl)-methyl-amino]-pyrrolidine-2-carboxylic acid To a solution of above product (1.2 g, 3 mmol) in THF (2 ml) and water (10 ml), LiOH (0.63 g, 15 mmol) was added, and the resulting suspension was stirred at room temperature for 5 hours. After removal of THF, the aqueous solution was extracted two times with Et$_2$O (10 ml×2), and then acidified to PH6-7 with 1M HCl. The solid was collected and washed with water to afford title product (0.7 g) in 60% yield.
MS m/e=395.8 [M+H]$^+$.

e) 8-{2S,4S)-1-(3-Chloro-benzyl)-4-[(2,4-difluoro-benzyl)-methyl-amino]-pyrrolidine-2-carbonyl}-2-cyclohexyl-1,3,8-triaza-spiro[4.5]dec-1-en-4-one A mixture of the acid (1 mmol), 2-cyclohexyl-1,3,8-triaza-spiro[4.5]dec-1-en-4-one (2 mmol), TBTU (1.5 mmol) and DIPEA (3 mmol) in DCM (20 ml) was stirred overnight at room temperature. The desired product was obtained by preparative HPLC as colorless oil (73 mg) in 12% yield. MS m/e=613.2 [M+H]$^+$.

EXAMPLE 65

2-(4-{(2S,4S)-1-(3-Chloro-benzyl)-4-[(2,4-difluoro-benzyl)-methyl-amino]-pyrrolidine-2-carbonyl}-piperazin-1-yl)-benzonitrile As described for Example 64e, (2S,4S)-1-(3-Chloro-benzyl)-4-[(2,4-difluoro-benzyl)-methyl-amino]-pyrrolidine-2-carboxylic acid (1 mmol) was converted, using 2-piperazin-1-yl-benzonitrile instead of 2-cyclohexyl-1,3,8-triaza-spiro[4.5]dec-1-en-4-one, to the title compound (51 mg) in 9% yield as colorless oil. MS m/e=565.1 [M+H]$^+$.

EXAMPLE 66

{(2S,4S)-1-(3-Chloro-benzyl)-4-[(2,4-difluoro-benzyl)-methyl-amino]-pyrrolidin-2-yl}-[4-(2-methoxy-phenyl)-piperazin-1-yl]-methanone As described for Example 64e, (2S,4S)-1-(3-chloro-benzyl)-4-[(2,4-difluoro-benzyl)-methyl-amino]-pyrrolidine-2-carboxylic acid (1 mmol) was converted, using 1-(2-methoxy-phenyl)-piperazine instead of 2-cyclohexyl-1,3,8-triaza-spiro[4.5]dec-1-en-4-one, to the title compound (40 mg) in 7% yield as colorless oil. MS m/e=570.1 [M+H]$^+$.

EXAMPLE 67

2-Cyclohexyl-8-{(2S,4S)-1-(3,4-dichloro-benzyl)-4-[(2,4-difluoro-benzyl)-methyl-amino]-pyrrolidine-2-carbonyl}-1,3,8-triaza-spiro[4.5]dec-1-en-4-one a) (2S,4R)-1-(3,4-Dichloro-benzyl)-4-hydroxy-pyrrolidine-2-carboxylic acid methyl ester As described for Example 64a, 4-hydroxy-pyrrolidine-2-carboxylic acid methyl ester (10 mmol) was converted, using 1,2-dichloro-4-chloromethyl-benzene instead of 1-chloro-3-chloromethyl-benzene, to the title compound (2.14 g) in 70% yield as yellow oil.
MS m/e=305.2 [M+H]$^+$.

b) (S)-1-(3,4-Dichloro-benzyl)-4-oxo-pyrrolidine-2-carboxylic acid methyl ester

As described for Example 64b, (2S,4R)-1-(3,4-dichloro-benzyl)-4-hydroxy-pyrrolidine-2-carboxylic acid methyl ester (7 mmol) was converted to the title compound (2.12 g) in 100% yield as yellow oil. MS m/e=303.2 [M+H]$^+$.

c) (2S,4S)-1-(3,4-Dichloro-benzyl)-4-[(2,4-difluoro-benzyl)-methyl-amino]-pyrrolidine-2-carboxylic acid methyl ester As described for Example 64b, (S)-1-(3,4-dichloro-benzyl)-4-oxo-pyrrolidine-2-carboxylic acid methyl ester (7 mmol) was converted to the title compound (2.8 g) in 90% yield as yellow oil. MS m/e=444.3 [M+H]$^+$.

d) (2S,4S)-1-(3,4-Dichloro-benzyl)-4-[(2,4-difluoro-benzyl)-methyl-amino]-pyrrolidine-2-carboxylic acid As described for Example 64d, (2S,4S)-1-(3,4-dichloro-benzyl)-4-[(2,4-difluoro-benzyl)-methyl-amino]-pyrrolidine-2-carboxylic acid methyl ester (6.3 mmol) was converted to title compound (1.63 g) in 60% yield as white solid. MS m/e=430.3 [M+H]$^+$.

e) 2-Cyclohexyl-8-{(2S,4S)-1-(3,4-dichloro-benzyl)-4-[(2,4-difluoro-benzyl)-methyl-amino]-pyrrolidine-2-carbonyl}-1,3,8-triaza-spiro[4.5]dec-1-en-4-one As described for Example 64e, (2S,4S)-1-(3,4-dichloro-benzyl)-4-[(2,4-difluoro-benzyl)-methyl-amino]-pyrrolidine-2-carboxylic acid (1 mmol) was converted, using 2-cyclohexyl-1,3,8-triaza-spiro[4.5]dec-1-en-4-one to the title compound (38.8 mg) by preparative HPLC in 6% yield as colorless oil. MS m/e=647.6 [M+H]$^+$.

EXAMPLE 68

[(2S,4S)-4-[(3,5-Bis-trifluoromethyl-benzyl)-methyl-amino]-1-(3-chloro-benzyl)-pyrrolidin-2-yl]-[4-(3-trifluoromethyl-phenyl)-piperazin-1-yl]-methanone a) (2S,4S)-4-[(3,5-Bis-trifluoromethyl-benzyl)-methyl-amino]-1-(3-chloro-benzyl)-pyrrolidine-2-carboxylic acid methyl ester As described for Example 64c, (S)-1-(3-chloro-benzyl)-4-oxo-pyrrolidine-2-carboxylic acid methyl ester (7 mmol) was converted, using (3,5-bis-trifluoromethyl-benzyl)-methyl-amine instead of (2,4-difluorobenzyl)-methyl-amine, to the title product in 95% yield as yellow oil. MS m/e=509.9 [M+H]$^+$.

b) (2S,4S)-4-[(3,5-Bis-trifluoromethyl-benzyl)-methyl-amino]-1-(3-chloro-benzyl)-pyrrolidine-2-carboxylic acid As described for Example 64d, (2S,4S)-4-[(3,5-bis-trifluoromethyl-benzyl)-methyl-amino]-1-(3-chloro-benzyl)-pyrrolidine-2-carboxylic acid was obtained in 65% yield as white solid. MS m/e=495.9 [M+H]$^+$.

c) [(2S,4S)-4-[(3,5-Bis-trifluoromethyl-benzyl)-methyl-amino]-1-(3-chloro-benzyl)-pyrrolidin-2-yl]-[4-(3-trifluoromethyl-phenyl)-piperazin-1-yl]-methanone As described for Example 64e, [(2S,4S)-4-[(3,5-bis-trifluoromethyl-benzyl)-methyl-amino]-1-(3-chloro-benzyl)-pyrrolidine-2-carboxylic acid (1 mmol) was converted, using 4-(3-trifluoromethyl-phenyl)-piperazine instead of 2-cyclohexyl-1,3,8-triaza-spiro[4.5]dec-1-en-4-one, to the title product (71 mg) in 10% yield as colorless oil. MS m/e=708.1 [M+H]$^+$.

EXAMPLE 69

2-{4-[4-[(3,5-Bis-trifluoromethyl-benzyl)-methyl-amino]-1-(3-chloro-benzyl)-pyrrolidine-2-carbonyl]-piperazin-1-yl}-benzonitrile As described for Example 64e, (2S,4S)-4-[(3,5-bis-trifluoromethyl-benzyl)-methyl-amino]-1-(3-chloro-benzyl)-pyrrolidine-2-carboxylic acid (1 mmol) was converted, using 2-piperazin-1-yl-benzonitrile instead of 2-cyclohexyl-1,3,8-triaza-spiro[4.5]dec-1-en-4-one, to the title compound (73.1 mg) in 111% yield as colorless oil.

MS m/e=665.1 [M+H]$^+$.

EXAMPLE 70

[(2S,4S)-4-[(3,5-Bis-trifluoromethyl-benzyl)-methyl-amino]-1-(3-chloro-benzyl)-pyrrolidin-2-yl]-[4-(2-fluoro-phenyl)-piperazin-1-yl]-methanone As described for Example 64e, (2S,4S)-4-[(3,5-bis-trifluoromethyl-benzyl)-methyl-amino]-1-(3-chloro-benzyl)-pyrrolidine-2-carboxylic acid (μmol) was converted, using 1-(2-fluoro-phenyl)-piperazine instead of 2-cyclohexyl-1,3,8-triaza-spiro[4.5]dec-1-en-4-one, to the title compound (72 mg) in 11% yield as colorless oil.

MS m/e=658.1 [M+H]$^+$.

EXAMPLE 71

[(2S,4S)-4-[(3,5-Bis-trifluoromethyl-benzyl)-methyl-amino]-1-(3-chloro-benzyl)-pyrrolidin-2-yl]-[4-(2-methoxy-phenyl)-piperazin-1-yl]-methanone As described for Example 64e, (2S,4S)-4-[(3,5-bis-trifluoromethyl-benzyl)-methyl-amino]-1-(3-chloro-benzyl)-pyrrolidine-2-carboxylic acid (1 mmol) was converted, using 1-(2-methoxy-phenyl)-piperazine instead of 2-cyclohexyl-1,3,8-triaza-spiro[4.5]dec-1-en-4-one, to the title compound (53.6 mg) in 8% yield as colorless oil.

MS m/e=670.1 [M+H]$^+$.

EXAMPLE 72

[(2S,4S)-4-[(3,5-Bis-trifluoromethyl-benzyl)-methyl-amino]-1-(3-chloro-benzyl)-pyrrolidin-2-yl]-(4-m-tolyl-piperazin-1-yl)-methanone As described for Example 64e, (2S,4S)-4-[(3,5-bis-trifluoromethyl-benzyl)-methyl-amino]-1-(3-chloro-benzyl)-pyrrolidine-2-carboxylic acid (1 mmol) was converted, using 4-m-tolyl-piperazine instead of 2-cyclohexyl-1,3,8-triaza-spiro[4.5]dec-1-en-4-one, to the title compound (52.3 mg) in 8% yield as colorless oil. MS m/e=654.1 [M+H]$^+$.

EXAMPLE 73

2-{4-[(2S,4S)-4-[(3,5-Bis-trifluoromethyl-benzyl)-methyl-amino]-1-(4-chloro-benzyl)-pyrrolidine-2-carbonyl]-piperazin-1-yl}-benzonitrile As described for Example 64e, (2S,4S)-4-[(3,5-bis-trifluoromethyl-benzyl)-methyl-amino]-1-(4-chloro-benzyl)-pyrrolidine-2-carboxylic acid (1 mmol) was converted, using 2-piperazin-1-yl-benzonitrile instead of 2-cyclohexyl-1,3,8- triaza-spiro[4.5]dec-1-en-4-one, to the title compound (60 mg) in 9% yield as colorless oil. MS m/e=665.1 [M+H]+.

EXAMPLE 74

[(2S,4S)-4-[(3,5-Bis-trifluoromethyl-benzyl)-methyl-amino]-1-(4-chloro-benzyl)-pyrrolidin-2-yl]-[4-(3-trifluoromethyl-phenyl)-piperazin-1-yl]-methanone As described for Example 64e, (2S,4S)-4-[(3,5-bis-trifluoromethyl-benzyl)-methyl-amino]-1-(4-chloro-benzyl)-pyrrolidine-2-carboxylic acid (1 mmol) was converted, using 1-(3-trifluoromethyl-phenyl)-piperazine instead of 2-cyclohexyl-1,3,8-triaza-spiro[4.5]dec-1-en-4-one, to the title compound (70.8 mg) in 10% yield as colorless oil. MS m/e=708.1 [M+H]+.

EXAMPLE 75

2-(4-{(2S,4S)-1-Benzyl-4-[(3,4-dichloro-benzyl)-methyl-amino]-pyrrolidine-2-carbonyl}-piperazin-1-yl)-benzonitrile a) (2S,4S)-1-Benzyl-4-[methyl-(2,2,2-trichloro-ethoxycarbonyl)-amino]-pyrrolidine-2-carboxylic acid To a solution of (2S,4S)-1-benzyl-4-[methyl-(2,2,2-trichloro-ethoxycarbonyl)-amino]-pyrrolidine-2-carboxylic acid methyl ester (6.4 mmol) in 18 mL of THF and 12 mL of methanol was added a solution of NaOH (12.8 mmol) in 10 mL water, and the reaction mixture was stirred overnight. The solution was diluted with 40 mL of water and extracted with 20 mL of EA. The aqueous layer was separated and acidified with 2N HCl to PH=5-6. Then the solution was extracted with EA (3×40 mL). The combined organic layers were washed by brine (20 mL), dried over Na2SO4, and concentrated to give 2.6 g of title product in 91% yield. MS m/e=410.4 [M+H]+.

b) (1-Benzyl-5-{1-[4-(2-cyano-phenyl)-piperazin-1-yl]-carbonyl}-pyrrolidin-3-yl)-methyl-carbamic acid 2,2,2-trichloro-ethyl ester A mixture of 1-benzyl-4-[methyl-(2,2,2-trichloro-ethoxycarbonyl)-amino]-pyrrolidine-2-carboxylic acid (3.4 mmol), 2-piperazin-1-yl-benzonitrile (5.1 mmol), EDC (6.8 mmol) and HOBT (6.8 mmol) in 15 mL of CH2Cl2 was stirred for 5 min, then 1 mL of Et3N was added, and the reaction mixture was stirred at rt for 12 h. After purification by chromagraphy on silica gel, 1.85 g of title product was obtained in 93% yield as yellow oil. MS m/e=579.4 [M+H]+.

c) 2-[4-(1-Benzyl-4-methylamino-pyrrolidine-2-carbonyl)-piperazin-1-yl]-benzonitrile To a mixture of (1-benzyl-5-{1-[4-(2-cyano-phenyl)-piperazin-1-yl]-carbonyl]}-pyrrolidin-3-yl)-methyl-carbamic acid 2,2,2-trichloro-ethyl ester (2.7 mmol) and Zn (8.3 mmol) in 20 mL of CH2Cl2 was added 5 drop of AcOH, and the mixture was stirred for 2 h. After removal of the Zn power, the crude product was purified by chromagraphy on silica gel to afford 1 g of title product as yellow oil in 95% yield. MS m/e=404.4 [M+H]+.

d) 2-(4-{1-Benzyl-4-[(3,4-dichloro-benzyl)-methyl-amino]-pyrrolidine-2-carbonyl}-piperazin-1-yl)-benzonitrile To a mixture of 2-[4-(1-benzyl-4-methylamino-pyrrolidine-2-carbonyl)-piperazin-1-yl]-benzonitrile (0.1 mmol) and 3,4-dichloro-benzaldehyde (0.15 mmol) in 2 mL of CH2Cl2 stirring at rt, was added NaBH(OAc)3 (0.15 mmol) and NEt3 (0.3 mmol), and then the resulting mixture was stirred overnight. After purification through preparative HPLC, 2.5 mg of 2-(4-{1-benzyl-4-[(3,4-dichloro-benzyl)-methyl-amino]-pyrrolidine-2-carbonyl}-piperazin-1-yl)-benzonitrile was obtained as colorless oil in 4.8% yield. MS m/e=562.4 [M+H]+.

EXAMPLE 76

2-(4-{(2S,4S)-1-Benzyl-4-[(3-chloro-4-fluoro-benzyl)-methyl-amino]-pyrrolidine-2-carbonyl}-piperazin-1-yl)-benzonitrile As described for Example 75d, 2-[4-(1-benzyl-4-methylamino-pyrrolidine-2-carbonyl)-piperazin-1-yl]-benzonitrile was converted, using 3-chloro-4-fluorobenzaldehyde instead of 3,4-dichlorobenzaldehyde, to the title compound. MS m/e=546.3 [M+H]+.

EXAMPLE 77

2-(4-{(2S,4S)-1-Benzyl-4-[(2-chlorobenzyl)-methyl-amino]-pyrrolidine-2-carbonyl}-piperazin-1-yl)-benzonitrile As described for Example 75d, 2-[4-(1-benzyl-4-methylamino-pyrrolidine-2-carbonyl)-piperazin-1-yl]-benzonitrile was converted, using 2-chlorobenzaldehyde instead of 3,4-dichlorobenzaldehyde, to the title compound. MS m/e=528.4 [M+H]+.

EXAMPLE 78

2-(4-{(2S,4S)-1-Benzyl-4-[(3-fluorobenzyl)-methyl-amino]-pyrrolidine-2-carbonyl}-piperazin-1-yl)-benzonitrile As described for Example 75d, 2-[4-(1-benzyl-4-methylamino-pyrrolidine-2-carbonyl)-piperazin-1-yl]-benzonitrile was converted, using 3-fluorobenzaldehyde instead of 3,4-dichlorobenzaldehyde, to the title compound. MS m/e=512.5 [M+H]+.

EXAMPLE 79

2-(4-{1-Benzyl-4-[methyl-(3-trifluoromethyl-benzyl)-amino]-pyrrolidine-2-carbonyl}-piperazin-1-yl)-benzonitrile As described for example 75d, 2-[4-(1-benzyl-4-methylamino-pyrrolidine-2-carbonyl)-piperazin-1-yl]-benonitrile was converted, using 3-(trifluoromethyl)benzaldehyde instead of 3,4-dichlorobenzaldhyde, to the title compound. MS m/e=562.5 [M+H]+.

EXAMPLE 80

2-(4-{1-Benzyl-4-[(2-chloro-5-trifluoromethyl-benzyl)-methyl-amino]-pyrrolidine-2-carbonyl}-piperazin-1-yl)-benzonitrile A mixture of 2-[4-(1-benzyl-4-methylamino-pyrrolidine-2-carbonyl)-piperazin-1-yl]-benzonitrile (0.1 mmol), 1-bromomethyl-2-chloro-5-trifluorobenzene (0.1 mmol) and NaOH (0.2 mmol) in 2 ml of dry DMF was stirred overnight and subsequently subjected to preparative HPLC purification on reversed phase eluting with an acetonitrile/water (0.05% $NEt_3$) gradient. 12.2 mg of the title compound was obtained in 21.4% yield as yellow powder. MS m/e=569.4 ([M+H]$^+$.

EXAMPLE 81

2-(4-{1-Benzyl-4-[(3-bromo-benzyl)-methyl-amino]-pyrrolidine-2-carbonyl}-piperazin-1-yl)-benzonitrile a) 1-Benzyl-4-[(3-bromo-benzyl)-methyl-amino]-pyrrolidine-2-carboxylic acid To a solution of 1-benzyl-4-oxo-pyrrolidine-2-carboxylic acid methyl ester (1 mmol), (3-bromo-benzyl)-methyl-amine (1 mmol) in 2 mL of $CH_2Cl_2$ were added $NaBH(OAc)_3$ (2 mmol) and 5 drops of AcOH, and the resulting mixture was stirred for 3 h. The mixture was treated with aq. $NaHCO_3$, extracted by $CH_2Cl_2$ (3×5 mL), and the combined extracts were washed by brine (10 mL), dried over $Na_2SO_4$, and concentrated to give 261.3 mg of crude product in 65% yield.
MS m/e=403.3 [M+H]$^+$.

b) 2-(4-{1-Benzyl-4-[(3-bromo-benzyl)-methyl-amino]-pyrrolidine-2-carbonyl}-piperazin-1-yl)-benzonitrile To a stirring mixture of 1-benzyl-4-[(3-bromo-benzyl)-methyl-amino]-pyrrolidine-2-carboxylic acid (0.2 mmol), EDC (0.3 mmol) and HOBT (0.3 mmol) in 3 mL of dry DMF were added 2-piperazin-1-yl-benzonitrile (0.24 mmol) and $NEt_3$ (0.6 mmol), and the reaction mixture was stirred overnight and subsequently subjected to preparative HPLC purification on reversed phase eluting with a acetonitrile/water (0.05% $NEt_3$) gradient. 17.5 mg of title product was obtained in 15.2% yield as brown oil.
MS m/e=574.3 [M+H]$^+$.

EXAMPLE 82

2-(4-{1-Benzyl-4-[(4-fluoro-benzyl)-methyl-amino]-pyrrolidine-2-carbonyl}-piperazin-1-yl)-benzonitrile As described for Example 81, 1-benzyl-4-oxo-pyrrolidine-2-carboxylic acid methyl ester was converted, using (4-fluoro-benzyl)-methyl-amine instead of (3-bromo-benzyl)-methyl-amine, to the title product. MS m/e=512.4 [M+H]$^+$.

EXAMPLE 83

2-(4-{1-Benzyl-4-[(2-bromo-benzyl)-methyl-amino]-pyrrolidine-2-carbonyl}-piperazin-1-yl)-benzonitrile As described for Example 81, 1-benzyl-4-oxo-pyrrolidine-2-carboxylic acid methyl ester was converted, using (2-bromo-benzyl)-methyl-amine instead of (3-bromo-benzyl)-methyl-amine, to the title product. MS m/e=574.3 [M+H]$^+$.

EXAMPLE 84

2-(4-{1-Benzyl-4-[(4-bromo-benzyl)-methyl-amino]-pyrrolidine-2-carbonyl}-piperazin-1-yl)-benzonitrile As described for Example 81, 1-benzyl-4-oxo-pyrrolidine-2-carboxylic acid methyl ester was converted, using (4-bromo-benzyl)-methyl-amine instead of (3-bromo-benzyl)-methyl-amine, to the title product. MS m/e=574.3 [M+H]$^+$.

EXAMPLE 85

[(2S,4R)-1-Benzyl-4-(2,4-difluoro-benzylamino)-pyrrolidin-2-yl]-[4-(2-methoxy-phenyl)-piperazin-1-yl]-methanone a) (2S,4S)-4-Iodo-pyrrolidine-1,2-dicarboxylic acid 1-tert-butyl ester 2-methyl ester To a round-bottom flask equipped with a magnetic stir bar and an addition funnel under $N_2$ was added N-Boc-L-trans-4-hydroxy-proline methyl ester (60 mmol, 1 equiv), $P(Ph)_3$ (72 mmol, 1.2 equiv) and anhydrous THF (275 ml). The solution was cooled to 0 centigrade, DEAD (1.2 equiv) in dry THF was added dropwise; followed by the addition of MeI (1.2 equiv). Upon addition of MeI, the solution turned from dark brown to bright yellow. The reaction mixture was allowed to warm to ambient temperature and stirred for 10 hours. The solvent was removed under reduced pressure and the crude oil was purified by chromatography on silica gel to afford title product (19.44 g) as colorless oil in 91% yield. MS m/e=356.4 [M+H]$^+$.

b) (2S,4R)-4-Azido-pyrrolidine-1,2-dicarboxylic acid 1-tert-butyl ester 2-methyl ester To a solution of 4-iodo-pyrrolidine-1,2-dicarboxylic acid 1-tert-butyl ester 2-methyl ester (20 mmol, 1 equiv) in DMF was added $NaN_3$ (2.5 equiv, 50 mmol), the resulting mixture was heated to 65 centigrade and stirred overnight. The mixture was diluted with water, extracted with AcOEt and dried over $Na_2SO_4$. After removal of solvent, the residue was purified by chromatography on silica gel to give title product (4.94 g) as colorless oil in 90% yield. MS m/e=271.5 [M+H]$^+$.

c) (2S,4R)-4-Amino-pyrrolidine-1,2-dicarboxylic acid 1-tert-butyl ester 2-methyl ester A solution of 4-azido-pyrrolidine-1,2-dicarboxylic acid 1-tert-butyl ester 2-methyl ester (838 mg, 2.2 mmol), THF (10 ml) and $P(Ph)_3$ (1.15 g, 4.4 mmol) and water (0.08 ml, 4.4 mmol) was refluxed for 6 hours and then concentrated in vacuo. The residue was dissolved in $Et_2O$ and treated with HCl (0.1N, 20 ml). The aqueous layer was extracted with $Et_2O$, washed with $Na_2CO_3$ (10% aq.), dried over anhydrous $MgSO_4$ and concentrated to afford the amine as colorless oil which was used in next step without further purification.

d) (2S,4R)-4-(2,4-Difluoro-benzylamino)-pyrrolidine-1,2-dicarboxylic acid 1-tert-butyl ester 2-methyl ester To a solution of 4-amino-pyrrolidine-1,2-dicarboxylic acid 1-tert-butyl ester 2-methyl ester (2 mmol, 1 equvi) was dissolved in dry DCM (20 ml) cooled to 0 centigrade was added 2,4-difluorobenzaldehyde (1.05 equiv), then NaBH(OAc)$_3$ (2 equiv) and 5 drops of HOAc. The mixture was warmed to room temperature and stirred overnight. The mixture was diluted with DCM, washed with brine, and dried over anhydrous sodium sulfate. After removal of solvent, the crude product was used for the next step without further purification. MS m/e=371.4 [M+H]$^+$.

e) (2S,4R)-4-[(2,4-Difluoro-benzyl)-Troc-amino]-pyrrolidine-1,2-dicarboxylic acid 1-tert-butyl ester 2-methyl ester To a solution of 4-(2,4-difluoro-benzylamino)-pyrrolidine-1,2-dicarboxylic acid 1-tert-butyl ester 2-methyl ester (2 mmol, 1 equiv) in DCM and cooled to 0 centigrade was added TrocCl (1.5 equiv) dropwise and followed by Et$_3$N (2 equiv). The mixture was stirred overnight at room temperature and concentrated. The residue was purified by chromatography on silica gel to give the product (1.0 g) as colorless oil in 92% yield.
MS m/e=545.3 [M+H]$^+$.

f) (2S,4R)-4-[(2,4-Difluoro-benzyl)-Troc-amino]-pyrrolidine methyl ester

To a solution of 4-[(2,4-difluoro-benzyl)-Troc-amino]-pyrrolidine-1,2-dicarboxylic acid 1-tert-butyl ester 2-methyl ester (1.5 mmol, 1 equiv) was in DCM (10 ml) cooled to 0 centigrade was added TFA (1.5 equiv). The mixture was stirred for 30 minutes, washed with NaHCO$_3$ and dried over Na$_2$SO$_4$. The organic layer was concentrated to give the crude product as oil for the next step without further purification.
MS m/e=445.5 [M+H]$^+$.

g) (2S,4R)-1-benzyl-4-[(2,4-Difluoro-benzyl)-Troc-amino]-pyrrolidine methyl ester To a solution of 4-[(2,4-difluoro-benzyl)-Troc-amino]-pyrrolidine methyl ester (1.5 mmol, 1 equvi) in dry DCM (20 ml) cooled to 0 centigrade was added benzaldehyde(1.2 equiv), NaBH(OAc)$_3$ (2 equiv) and 5 drops of HOAc. The resulting mixture was warmed to room temperature and stirred overnight. The reaction solution was washed with brine, dried over anhydrous sodium sulfate and concentrated to give the crude product which was used for next step without further purification. MS m/e=535.4 [M+H]$^+$.

h) (2S,4R)-1-benzyl-4-[(2,4-Difluoro-benzyl)-Troc-amino]-pyrrolidine

To a solution of 1-benzyl-4-[(2,4-difluoro-benzyl)-Troc-amino]-pyrrolidine methyl ester (1.5 mmol, 1 equiv) in methanol (10 ml) was added LiOH (5 equiv). The mixture was stirred overnight, acidified to PH=5, and extracted with DCM. The organic layer was dried, and concentrated to give the crude product which was used for next step without further purification.
MS m/e=519.2 [M−H]$^-$.

i) {(2S,4R)-1-Benzyl-[4-(2,4-difluoro-benzyl)-Troc-aminol]-pyrrolidin-2-yl}-[4-(2-methoxy-phenyl)-piperazin-1-yl]-methanone A mixture of 1-benzyl-4-[(2,4-difluoro-benzyl)-Troc-amino]-pyrrolidine (1.5 mmol, 1 equiv), EDCI (1.1 equiv), HOBt (1.1 equiv), Et$_3$N (1.5 equiv) and (1.1 equiv) 2-methoxy-phenylpiperazine in DCM was stirred at room temperature overnight. Concentration of the mixture gave the crude product for the next step. MS m/e=695.4 [M+H]$^+$.

j) [(2S,4R)-1-Benzyl-4-(2,4-difluoro-benzylamino)-pyrrolidin-2-yl]-[4-(2-methoxy-phenyl)-piperazin-1-yl]-methanone To a solution of {1-benzyl-[4-(2,4-difluoro-benzyl)-Troc-amino]-pyrrolidin-2-yl}-[4-(2-methoxy-phenyl)-piperazin-1-yl]-methanone (0.2 mmol, 1 equiv) in MeOH was added Zn dust (2 mmol, 10 equiv) and 5 drops of HOAc, and the mixture was refluxed overnight. The final product (11.9 mg) was obtained as white powder by prepared HPLC in 11% yield. MS m/e=521.5 [M+H]$^+$.

EXAMPLE 86

[(2S,4R)-1-Benzyl-4-(2,4-difluoro-benzylamino)-pyrrolidin-2-yl]-[4-(2-fluorophenyl)-piperazin-1-yl]-methanone As described for Example 85, using 2-fluorophenylpiperazine instead of 2-methoxy-phenylpiperazine, the title compound (3.6 mg) was obtained as white powder.
MS m/e=509.4 [M+H]$^+$.

EXAMPLE 87

[(2S,4R)-1-Benzyl-4-(2,4-difluoro-benzylamino)-pyrrolidin-2-yl]-[4-(3-trifluoromethyl-phenyl)-piperazin-1-yl]-methanone As described for Example 85, using 3-trifluoromethyl-phenylpiperazine instead of 2-methoxy-phenylpiperazine, the title compound (5.0 mg) was obtained as white powder. MS m/e=559.5 [M+H]$^+$.

EXAMPLE 88

2-{4-[(2S,4R)-1-Benzyl-4-(2,4-difluoro-benzylamino)-pyrrolidine-2-carbonyl]-piperazin-1-yl}-benzonitrile As described for Example 85, using 2-cyano-phenylpiperazine instead of 2-methoxy-phenylpiperazine, the title compound (6.8 mg) was obtained as white powder.
MS m/e=516.4 [M+H]$^+$.

EXAMPLE 89

N-{(3S,5S)-1-benzyl-5-[4-(2-cyano-phenyl)-piperazine-1-carbonyl]-pyrrolidin-3-yl}-2-chloro-benzamide a) 1-Benzyl-4-tert-butoxybonylamino-pyrrolidine-2-carboxylic methyl ester

To a solution of 4-azido-1-benzyl-pyrrolidine-2-carboxylic acid methyl ester (4.36 g, 16.8 mmol) in THF (30 mL) was added triphenylphosphine (8.81 g, 33.6 mmol) and water (0.756 g, 42 mmol) under inter atmosphere. The mixture was refluxed with stirring for 6 h. After removal of THF, the residue was dissolved in Et$_2$O, treated with 0.15 N aqueous HCl, stirred for another 5 min. The solution was extracted with Et$_2$O twice, then the aqueous layer was neutralized with 10% NaHCO$_3$ until PH>10, and extracted with DCM. The solvent was removed to afford a yellow oil, which was then dissolved in H₂O (20 mL), treated with (Boc)₂O (2.6 g, 12.3 mmol), and stirred overnight. The product was extracted into EA, which was washed with water and brine, dried, and concentrated to afford the title product 1-benzyl-4-tert-butoxybonylamino-pyrrolidine-2-carboxylic methyl ester 3.15 g (59%) as a yellow oil. MS m/e=335.2 [M+H]⁺.

b) 1-Benzyl-4-tert-butoxybonylamino-pyrrolidine-2-carboxylic acid

Benzyl-4-tert-butoxybonylamino-pyrrolidine-2-carboxylic methyl ester (3 g, 8.97 mmol) and LiOH (1.8 g, 43,9 5 mmol) were dissolved in THF/H₂O (40 mL), and the resulting mixture was stirred for 5 hours at room temperature. After removal of THF, the PH was adjusted to 6-7. The solid was collected and dried to afford title product 1-benzyl-4-tert-butoxybonylamino-pyrrolidine-2-carboxylic acid 2.2 g (78%) as white solid.
MS m/e=321.2 [M+H]⁺ c) {1-Benzyl-5-[4-(2-cyano-phenyl)-piperzine-1-carbonyl]-pyrrolidine-3-yl}carbamic acid tert-butyl ester The mixture of 1-benzyl-4-tert-butoxybonylamino-pyrrolidine-2-carboxylic acid (1.8 g, 5.62 mmol), 1-ethyl-3-(3-dimethylaminopropyl)-carbodiimidehydrochloride (2.15 g, 11.24 mmol), N-hydroxybenzotriazole (0.759 g, 5.62 mmol), 2-piperazin-1-yl-benzonitrile (1.58 g, 8.43 mmol) and triethylamine (1.7 g, 16.86 mmol) in dry DCM (10 mL) was stirred overnight. The crude product was purified by column chromatography (hexan/AcOEt=4:1) to afford the title product {1-benzyl-5-[4-(2-cyano-phenyl)-piperazine-1-carbonyl]-pyrrolidine-3-yl}carbamic acid tert-butyl ester 2 g (74%) as white solid. MS m/e=490.2 [M+H]⁺ d) 2-[4-(4-Amino-1-benzyl-pyrrolidine-2-carbonyl)-piperazin-1-yl]-benzonitrile {1-Benzyl-5-[4-(2-cyano-phenyl)-piperazine-1-carbonyl]-pyrrolidine-3-yl}carbamic acid tert-butyl ester (2 g, 4 mmol) was dissolved in 15 mL DCM/CF₃COOH (2:1), stirred overnight. After removal of solvent, the residue was treated with saturated NaHCO₃, extracted with EA (2×100 mL). The organic layer was dried over Na₂SO₄, concentrated to afforded title product 2-[4-(4-amino-1-benzyl-pyrrolidine-2-carbonyl)-piperazin-1-yl]-benzonitrile 1.6 g (100%) as brown oil. MS m/e=390.2 [M+H]⁺.

e) N-{(3S,5S)-1-Benzyl-5-[4-(2-cyano-phenyl)-piperazine-1-carbonyl]-pyrrilidin-3-yl}-2-chloro-benzamide To a mixture of 2-[4-(4-amino-1-benzyl-pyrrolidine-2-carbonyl)-piperazin-1-yl]-benzonitrile and 2-chloro-benzoyl chloride in DCM (1 mL), triethylamine (0.384 mmol) was added, and the resulting mixture was stirred overnight and then concentrated. The residue was purified by preparative HPLC on reversed phase eluting with an acetonitrile/water [0.1% aq NH₃ (25%)] gradient to afford the title compound (6.7 mg, 9.9%) as a light yellow oil. MS m/e=528.3 [M+H]⁺.

EXAMPLE 90

N-{(3S,5S)-1-Benzyl-5-[4-(2-cyano-phenyl)-piperazine-1-carbonyl]-pyrrolidin-3-yl}-3,5-dichloro-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 3,5-dichloro-benzoyl chloride instead of 2-chloro-benzoyl chloride, to the title compound (8.3 mg, 11.5%) as light yellow oil. MS m/e=562.2 [M+H]⁺.

EXAMPLE 91

N-{(3S,5S)-1-Benzyl-5-[4-(2-cyano-phenyl)-piperazine-1-carbonyl]-pyrrolidin-3-yl}-2,6-dichloro-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 2,6-dichloro-benzoyl chloride instead of 2-chloro-benzoyl chloride, to the title compound (15 mg, 20%) as light yellow oil. MS m/e=562.2 [M+H]⁺.

EXAMPLE 92

N-{(3S,5S)-1-Benzyl-5-[4-(2-cyano-phenyl)-piperazine-1-carbonyl]-pyrrolidin-3-yl}-3,4-dichloro-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 3,4-dichloro-benoyl chloride instead of 2-chloro-benzoyl chloride, to the title compound (13 mg, 18.1%) as light yellow oil. MS m/e=562.2 [M+H]⁺.

EXAMPLE 93

N-{(3S,5S)-1-Benzyl-5-[4-(2-cyano-phenyl)-piperazine-1-carbonyl]-pyrrolidin-3-yl}-3-methoxy-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 3-methoxy-benzoyl chloride instead of 2-chloro-benzoyl chloride, to the title compound (5.5 mg, 8.2%) as light yellow oil. MS m/e=524.3 [M+H]⁺.

EXAMPLE 94

N-{(3S,5S)-1-Benzyl-5-[4-(2-cyano-phenyl)-piperazine-1-carbonyl]-pyrrolidin-3-yl}-2-trifluoromethyl-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 2-trifluoromethyl-benzoyl chlordie instead of 2-chloro-benzoyl chloride, to the title compound (15.5 mg, 21.5%) as light yellow oil. MS m/e=561.6 [M+H]⁺.

EXAMPLE 95

N-{(3S,5S)-1-Benzyl-5-[4-(2-cyano-phenyl)-piperazine-1-carbonyl]-pyrrolidin-3-yl}-3-methyl-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 3-methyl-benzaoyl chloride instead of 2-chloro-benzoyl chloride, to the title compound (2.6 mg, 4%) as light yellow oil. MS m/e=507.6 [M+H]+.

EXAMPLE 96

N-{(3S,5S)-1-Benzyl-5-[4-(2-cyano-phenyl)-piperazine-1-carbonyl]-pyrrolidin-3-yl}-3,4,5-trimethoxy-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 3,4,5-trimethoxy-benzoyl chloride instead of 2-chloro-benzoyl chloride, to the title compound (13.4 mg, 17.9%) as light yellow oil. MS m/e=583.7 [M+H]+.

EXAMPLE 97

N-{(3S,5S)-1-Benzyl-5-[4-(2-cyano-phenyl)-piperazine-1-carbonyl]-pyrrolidin-3-yl}-3-chloro-benzamide As described for Example 89e, 2-[4-(4-amino-1benzyl-pyrrolidine-2-carbonyl)-piperazin-1-yl]-benzonitrile (50.0 mg, 0.128 mmol) was converted, using 3-chloro-benzoyl chloride instead of 2-chloro-benzoyl chloride, to the title compound (4.3 mg, 6.4%) as light yellow oil. MS m/e=528.3 [M+H]+.

EXAMPLE 98

N-{(3S,5S)-1-Benzyl-5-[4-(2-cyano-phenyl)-piperazine-1-carbonyl]-pyrrolidin-3-yl}-2-methoxy-benzamide As described for Example 89e, 2-[4-(4-amino-1-benzyl-pyrrolidine-2-carbonyl)-piperazin-1-yl]-benzonitrile (50.0 mg, 0.128 mmol) was converted, using 2-methoxy-benzoyl chloride instead of 2-chloro-benzoyl chloride, to the title compound (5.2 mg, 7.7%) as light yellow oil. MS m/e=524.3 [M+H]+.

The invention claimed is:

1. A compound of formula I

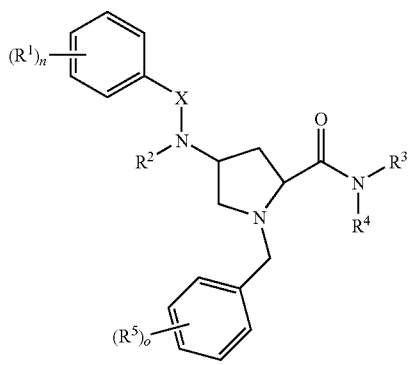

wherein
  $R^1$ is hydrogen, halogen, lower alkyl, lower alkyl substituted by halogen, lower alkoxy, or lower alkoxy substituted by halogen;
  $R^2$ is hydrogen or lower alkyl;
  $R^3$ and $R^4$ together with the N-atom to which they are attached form a non aromatic heterocyclic group, selected from

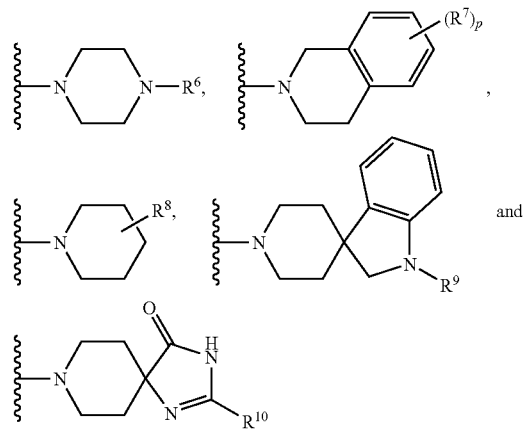

$R^5$ is hydrogen or halogen;
  $R^6$ is phenyl, unsubstituted or substituted by cyano, halogen, lower alkyl, lower alkoxy, $CF_3$, —$(CH_2)_2$O-lower alkyl, C(O)-lower alkyl or C(O)O-lower alkyl, or is pyridinyl, unsubstituted or substituted by $CF_3$, or is —C(O)-phenyl;
  $R^7$ is hydrogen or lower alkoxy;
  $R^8$ is phenyl, lower alkyl or —C(O)O-lower alkyl;
  $R^9$ is hydrogen or $S(O)_2$-lower alkyl;
  $R^{10}$ is hydrogen or cycloalkyl;
  X is —$CH_2$— or —C(O)—;
  p is 1 or 2;
  n is 1, 2 or 3; and
  o is 1 or 2;
or a pharmaceutically acceptable acid addition salt thereof.

2. A compound of claim 1, wherein X is —$CH_2$.

3. A compound of claim 2, wherein $R^3$ and $R^4$ together with the N-atom to which they are attached form a piperazine ring, which is substituted by $R^6$.

4. A compound of claim 3, wherein the $R^6$ is phenyl substituted by cyano.

5. A compound of claim 4, selected from the group consisting of
  2-{4-[(2S,4S)-1-benzyl-4-(2,4-difluoro-benzylamino)-pyrrolidine-2-carbonyl]-piperazin-1-yl}-benzonitrile,
  2-(4-{(2S,4S)-1-benzyl-4-[(3,5-bis-trifluoromethyl-benzyl)-methyl-amino]-pyrrolidine-2-carbonyl}-piperazin-1-yl)-benzonitrile,
  2-{4-[(2S,4S)-1-benzyl-4-(3,5-dimethoxy-benzylamino)-pyrrolidine-2-carbonyl]-piperazin-1-yl}-benzonitrile,
  2-{4-[(2S,4S)-1-benzyl-4-(2-trifluoromethyl-benzylamino)-pyrrolidine-2-carbonyl]-piperazin-1-yl}-benzonitrile,
  2-{4-[(2S,4S)-1-benzyl-4-(2-chloro-5-trifluoromethyl-benzylamino)-pyrrolidine-2-carbonyl]-piperazin-1-yl}-benzonitrile,
  2-{4-[(2S,4S)-1-benzyl-4-(3-chloro-benzylamino)-pyrrolidine-2-carbonyl]-piperazin-1-yl}-benzonitrile,
  2-{4-[(2S,4S)-1-benzyl-4-(3-chloro-4-fluoro-benzylamino)-pyrrolidine-2-carbonyl]-piperazin-1-yl}-benzonitrile,
  2-{4-[(2S,4S)-1-benzyl-4-(3,4-dichloro-benzylamino)-pyrrolidine-2-carbonyl]-piperazin-1-yl}-benzonitrile, 2-{4-[(2S,4S)-1-benzyl-4-(3-chloro-2-fluoro-benzylamino)-pyrrolidine-2-carbonyl]-piperazin-1-yl}-benzonitrile, 2-{4-[4-(2,4-difluoro-benzylamino)-1-(3-fluoro-benzyl)-pyrrolidine-2-carbonyl]-piperazin-1yl}-benzonitrile and 2-{4-[(2S,4R)-1-benzyl-4-(2,4-difluoro-benzylamino)-pyrrolidine-2-carbonyl]-piperazin-1-yl}-benzonitrile.

6. A compound of claim 3, wherein the R⁶— is phenyl substituted by CF₃.

7. A compound of claim 6, selected from the group consisting of

[(2S,4S)-1-benzyl-4-(2,4-difluoro-benzylamino)-pyrrolidin-2-yl]-[4-(3-trifluoromethyl-phenyl) -piperazin-1-yl]-methanone, {(2S,4S)-1-benzyl-4-[(3,5-bis-trifluoromethyl-benzyl)-methyl-amino]-pyrrolidin-2-yl}-[4-(3-trifluoromethyl-phenyl) -piperazin-1-yl]-methanone,

[(2S,4S)-4-[(3,5-bis-trifluoromethyl-benzyl)-methyl-amino]-1-(3-chloro-benzyl)-pyrrolidin-2-yl]-[4-(3-trifluoromethyl-phenyl)-piperazin-1-yl]-methanone and

[(2S,4R)-1-benzyl-4-(2,4-difluoro-benzylamino)-pyrrolidin-2-yl]-[4-(3-trifluoromethyl-phenyl) -piperazin-1-yl]-methanone.

8. A compound of claim 3, wherein the R⁶— is phenyl substituted by halogen.

9. A compound of claim 8, selected from the group consisting of

[(2S,4S)-1-benzyl-4-(2,4-difluoro-benzylamino)-pyrrolidin-2-yl]-[4-(4-fluoro-phenyl)-piperazin-1-yl]-methanone and

[(2S,4S)-1-benzyl-4-(2,4-difluoro-benzylamino)-pyrrolidin-2-yl]-[4-(2-chloro-phenyl)-piperazin -1-yl]-methanone.

10. A compound of claim 3, wherein the R⁶— is phenyl unsubstituted or substituted by lower alkoxy.

11. A compound of claim 10, selected from the group consisting of

[(2S,4S)-1-benzyl-4-(2,4-difluoro-benzylamino)-pyrrolidin-2-yl]-(4-phenyl-piperazin-1-yl)-methanone and

[(2S,4S)-1-benzyl-4-(2,4-difluoro-benzylamino)-pyrrolidin-2-yl]-[4-(2-methoxy-phenyl)-piperazin -1-yl]-methanone.

12. A compounds of claim 2, wherein R³ and R⁴ together with the N-atom to which they are attached form the group 3,4-dihydro-1H-isoquinoline, substituted by R⁷.

13. A compound of claim 12, wherein the compound is

[(2S,4S)-1-benzyl-4-(2,4-difluoro-benzylamino)-pyrrolidin-2-yl]-(6,7-dimethoxy-3,4-dihydro-1H-isoquinolin-2-yl)-methanone.

14. A compounds of claim 1, wherein X is —C(O)—.

15. A compound of claim 14, selected from the group consisting of

N-{(3S,5S)-1-benzyl-5-[4-(2-cyano-phenyl)-piperazine-1-carbonyl]-pyrrolidin-3-yl}-2-chloro-benzamide, N-{(3S,5S)-1-benzyl-5-[4-(2-cyano-phenyl)-piperazine-1-carbonyl]-pyrrolidin-3-yl}-3,5-dichloro-benzamide, N-{(3S,5S)-1-benzyl-5-[4-(2-cyano-phenyl)-piperazine-1-carbonyl]-pyrrolidin-3-yl}-2-trifluoromethyl -benzamide and N-{(3S,5S)-1-benzyl-5-[4-(2-cyano-phenyl)-piperazine-1-carbonyl]-pyrrolidin-3-yl}-2-methoxy -benzamide.

16. A pharmaceutical composition comprising a therapeutically effective amount of a compound of formula I

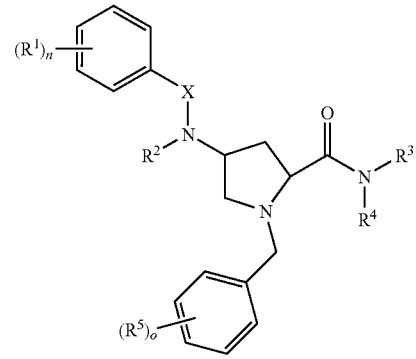

wherein
R¹ is hydrogen, halogen, lower alkyl, lower alkyl substituted by halogen, lower alkoxy, or lower alkoxy substituted by halogen;
R² is hydrogen or lower alkyl;
R³ and R⁴ together with the N-atom to which they are attached form a non aromatic heterocyclic group, selected from

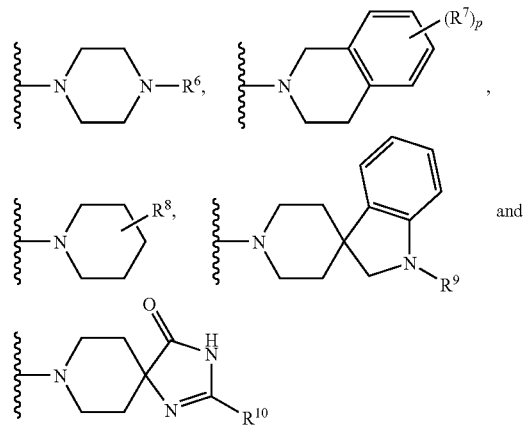

R⁵ is hydrogen or halogen;
R⁶ is phenyl, unsubstituted or substituted by cyano, halogen, lower alkyl, lower alkoxy, CF₃, —(CH₂)₂O-lower alkyl, C(O)-lower alkyl or C(O)O-lower alkyl, or is pyridinyl, unsubstituted or substituted by CF₃, or is —C(O)-phenyl;
R⁷ is hydrogen or lower alkoxy;
R⁸ is phenyl, lower alkyl or —C(O)O-lower alkyl;
R⁹ is hydrogen or S(O)₂-lower alkyl;
R¹⁰ is hydrogen or cycloalkyl;
X is —CH₂— or —C(O)—;
p is 1 or 2;
n is 1, 2 or 3; and
o is 1 or 2;
or a pharmaceutically acceptable acid addition salt thereof and a pharmaceutically acceptable carrier.

* * * * *